(12) United States Patent
Heil et al.

(10) Patent No.: US 9,893,292 B2
(45) Date of Patent: *Feb. 13, 2018

(54) MATERIALS FOR ORGANIC ELECTROLUMINESCENCE DEVICES

(71) Applicant: Merck Patent GmbH, Darmstadt (DE)

(72) Inventors: Holger Heil, Frankfurt am Main (DE); Arne Buesing, Frankfurt am Main (DE); Philipp Stoessel, Frankfurt am Main (DE); Horst Vestweber, Gilserberg (DE)

(73) Assignee: Merck Patent GmbH (DE)

( * ) Notice: Subject to any disclaimer, the term of this patent is extended or adjusted under 35 U.S.C. 154(b) by 975 days.

This patent is subject to a terminal disclaimer.

(21) Appl. No.: 14/219,793

(22) Filed: Mar. 19, 2014

(65) Prior Publication Data

US 2014/0203215 A1 Jul. 24, 2014

Related U.S. Application Data

(62) Division of application No. 11/916,070, filed as application No. PCT/EP2006/004609 on May 16, 2006, now Pat. No. 8,679,645.

(30) Foreign Application Priority Data

Jun. 9, 2005 (DE) .......................... 10 2005 026 651

(51) Int. Cl.
| | | |
|---|---|---|
| *H01L 51/00* | (2006.01) | |
| *C07C 13/465* | (2006.01) | |
| *C07C 13/48* | (2006.01) | |
| *C07C 13/58* | (2006.01) | |
| *C07C 13/605* | (2006.01) | |
| *C07C 23/18* | (2006.01) | |
| *C07C 25/22* | (2006.01) | |
| *C07C 211/54* | (2006.01) | |
| *C07C 211/56* | (2006.01) | |
| *C07D 237/08* | (2006.01) | |
| *C07D 237/26* | (2006.01) | |
| *C07D 241/38* | (2006.01) | |
| *C07D 319/18* | (2006.01) | |
| *C07D 471/04* | (2006.01) | |
| *C07D 471/08* | (2006.01) | |
| *C07D 487/04* | (2006.01) | |
| *C07D 487/08* | (2006.01) | |
| *C07D 493/06* | (2006.01) | |
| *C07D 493/08* | (2006.01) | |
| *C07F 7/08* | (2006.01) | |
| *C09K 11/06* | (2006.01) | |
| *H05B 33/14* | (2006.01) | |
| *H01L 51/50* | (2006.01) | |

(52) U.S. Cl.
CPC .......... *H01L 51/006* (2013.01); *C07C 13/465* (2013.01); *C07C 13/48* (2013.01); *C07C 13/58* (2013.01); *C07C 13/605* (2013.01); *C07C 23/18* (2013.01); *C07C 25/22* (2013.01); *C07C 211/54* (2013.01); *C07C 211/56* (2013.01); *C07D 237/08* (2013.01); *C07D 237/26* (2013.01); *C07D 241/38* (2013.01); *C07D 319/18* (2013.01); *C07D 471/04* (2013.01); *C07D 471/08* (2013.01); *C07D 487/04* (2013.01); *C07D 487/08* (2013.01); *C07D 493/06* (2013.01); *C07D 493/08* (2013.01); *C07F 7/0807* (2013.01); *C09K 11/06* (2013.01); *H01L 51/0052* (2013.01); *H01L 51/0054* (2013.01); *H01L 51/0058* (2013.01); *H01L 51/0059* (2013.01); *H01L 51/0072* (2013.01); *H05B 33/14* (2013.01); *C07C 2602/10* (2017.05); *C07C 2603/24* (2017.05); *C09K 2211/1011* (2013.01); *C09K 2211/1022* (2013.01); *H01L 51/0094* (2013.01); *H01L 51/5012* (2013.01); *H01L 51/5048* (2013.01); *H01L 51/5096* (2013.01); *Y02E 10/549* (2013.01)

(58) Field of Classification Search
CPC .................................................. H01L 51/0052
See application file for complete search history.

(56) References Cited

U.S. PATENT DOCUMENTS

| | | | |
|---|---|---|---|
| 4,539,507 | A | 9/1985 | VanSlyke et al. |
| 5,077,142 | A | 12/1991 | Sakon et al. |
| 5,151,629 | A | 9/1992 | VanSlyke |
| 5,648,021 | A | 7/1997 | Wingen et al. |
| 5,840,217 | A | 11/1998 | Lupo et al. |
| 5,935,721 | A | 8/1999 | Shi et al. |
| 6,458,909 | B1 | 10/2002 | Spreitzer et al. |
| 6,482,478 | B1 | 11/2002 | Wingen |

(Continued)

FOREIGN PATENT DOCUMENTS

| | | |
|---|---|---|
| EP | 0 676 461 A2 | 10/1995 |
| EP | 1182183 A1 | 2/2002 |

(Continued)

OTHER PUBLICATIONS

Machine translation of JP2001-332384. Date of publication: Nov. 20, 2001.

(Continued)

*Primary Examiner* — Alex A Rolland
(74) *Attorney, Agent, or Firm* — Drinker Biddle & Reath LLP

(57) ABSTRACT

The present invention relates to novel materials which can be used in organic electronic devices, in particular electroluminescent devices, and are certain derivatives of fused aromatic systems.

15 Claims, No Drawings

(56) References Cited

U.S. PATENT DOCUMENTS

| | | | |
|---|---|---|---|
| 8,679,645 B2 * | 3/2014 | Heil | C07C 13/465 257/40 |
| 8,785,001 B2 * | 7/2014 | Vestweber | C09K 11/06 257/40 |
| 2001/0037012 A1 * | 11/2001 | Towns | C08G 61/121 528/394 |
| 2002/0048687 A1 | 4/2002 | Hosokawa et al. | |
| 2003/0011886 A1 | 1/2003 | Chern et al. | |
| 2004/0020891 A1 | 2/2004 | Ishibashi et al. | |
| 2005/0064233 A1 | 3/2005 | Matsuura et al. | |
| 2005/0176952 A1 | 8/2005 | Tuan et al. | |
| 2005/0176953 A1 | 8/2005 | Tuan et al. | |
| 2005/0233165 A1 | 10/2005 | Ido et al. | |
| 2006/0033421 A1 | 2/2006 | Matsuura et al. | |
| 2006/0069287 A1 | 3/2006 | Kubo et al. | |
| 2006/0122688 A1 | 6/2006 | Shanley et al. | |
| 2006/0134456 A1 | 6/2006 | Ikeda et al. | |
| 2006/0154076 A1 | 7/2006 | Kubota et al. | |
| 2007/0059556 A1 | 3/2007 | Kim et al. | |
| 2007/0060736 A1 | 3/2007 | Becker et al. | |
| 2008/0107563 A1 | 5/2008 | Ivanine et al. | |
| 2008/0303422 A1 * | 12/2008 | Vestweber | C09K 11/06 313/504 |
| 2009/0026919 A1 | 1/2009 | Stossel et al. | |
| 2009/0079334 A1 | 3/2009 | Kim et al. | |

FOREIGN PATENT DOCUMENTS

| | | |
|---|---|---|
| JP | 6-211757 | 8/1994 |
| JP | 6-346049 | 12/1994 |
| JP | 2000053676 | 2/2000 |
| JP | 2001-332384 A | 11/2001 |
| JP | 2002063989 A | 2/2002 |
| JP | 2002-134276 A | 5/2002 |
| JP | 2003-55276 | 2/2003 |
| JP | 2005008600 | 1/2005 |
| JP | 2005008600 A * | 1/2005 |
| JP | 2005314239 | 11/2005 |
| JP | 2008522719 A | 7/2008 |
| JP | 2008531020 A | 8/2008 |
| JP | 2009502778 A | 1/2009 |
| JP | 2009508352 A | 2/2009 |
| WO | WO-98/27136 A1 | 6/1998 |
| WO | WO-0172673 A1 | 10/2001 |
| WO | WO-2004/013073 A1 | 2/2004 |
| WO | WO-2004/016575 A1 | 2/2004 |
| WO | WO-2004/018588 A1 | 3/2004 |
| WO | WO-2004/024670 A1 | 3/2004 |
| WO | WO-2005/014689 A2 | 2/2005 |
| WO | WO-2005121057 A1 | 12/2005 |

OTHER PUBLICATIONS

Machine translation of JP2002-063989. Date of publication: Feb. 28, 2002.

Machine translation of JP2003-055276. Date of publication: Feb. 26, 2003.

International Search Report for PCT/EP2006/004609, dated Sep. 13, 2006.

I. Agranat et al., Static and Dynamic Stereochemistry of a Chiral, Doubly Bridged 9,10-Diphenylanthracene from a Stereospecific Polycyclic Aromatic Dicarbonyl Coupling, J. Org. Chem., 55, pp. 4943-4950, 1990.

* cited by examiner

MATERIALS FOR ORGANIC ELECTROLUMINESCENCE DEVICES

RELATED APPLICATIONS

This application is a divisional application of U.S. application Ser. No. 11/916,070 filed May 8, 2008 which is incorporated by reference. U.S. application Ser. No. 11/916,070 is a national stage application (under 35 U.S.C. § 371) of PCT/EP2006/004609, filed May 16, 2006, which claims benefit of German application 10 2005 026 651.7, filed Jun. 9, 2005.

Organic semiconductors are used as functional materials in a number of different applications which can be ascribed to the electronics industry in the broadest sense. The general structure of organic electroluminescent devices (OLEDs) is described, for example, in U.S. Pat. Nos. 4,539,507, 5,151,629, EP 0676461 and WO 98/27136.

However, these devices still exhibit considerable problems which require urgent improvement: for example, the operating lifetime is still short, in particular in the case of blue emission, and consequently it has hitherto only been possible to implement simple applications commercially. Furthermore, the host materials in accordance with the prior art used for blue emitters, which frequently comprise fused aromatic systems, are often only sparingly soluble in common organic solvents, which makes their purification during the synthesis, but also the cleaning of the plants during production of the organic electronic devices more difficult.

As closest prior art, mention can be made of the use of various fused aromatic compounds, in particular anthracene or pyrene derivatives, as host materials, in particular for blue-emitting electroluminescent devices. The host material known from the prior art is 9,10-bis(2-naphthyl)anthracene (U.S. Pat. No. 5,935,721). Further anthracene derivatives which are suitable as host materials are described, for example, in WO 01/076323, in WO 01/021729, in WO 04/013073, in WO 04/018588, in WO 03/087023 or in WO 04/018587. Host materials based on aryl-substituted pyrenes and chrysenes are described in WO 04/016575, which in principle also encompasses corresponding anthracene and phenanthrene derivatives. WO 03/095445 and CN 1362464 describe 9,10-bis(1-naphthyl)anthracene derivatives for use in OLEDs. For high-quality applications, however, it is necessary to have improved host materials available. Particularly problematical is the poor solubility of many of the said systems in accordance with the prior art, which makes the preparation, purification and processing of the compounds more difficult.

The above-mentioned prior art confirms that the host material plays a crucial role in the functioning of organic electroluminescent devices. There thus continues to be a demand for improved materials, in particular host materials for blue-emitting OLEDs, which result in good efficiencies and at the same time in long lifetimes in organic electronic devices and have good solubility. Surprisingly, it has been found that organic electronic devices which comprise certain fused aromatic compounds which are substituted by aryl groups having fused cycloalkyl groups have significant improvements over the prior art. These materials enable an increase in the lifetime of the organic electronic device compared with materials in accordance with the prior art. In contrast to the purely aromatic compounds usually used or those which are substituted at most by short open-chain alkyl groups, for example methyl groups, the compounds according to the invention have high solubility in the organic solvents usually used. In contrast to compounds which are substituted by long open-chain alkyl groups, the compounds according to the invention can also be sublimed without problems. The present invention therefore relates to these materials and to the use thereof in organic electronic devices.

JP 2005/008600 describes 9,10-bis(5,6,7,8-tetrahydro-2-naphthyl)anthracene derivatives as host or as hole-transport compound in organic electronic devices. However, these compounds are not suitable for the production of dark-blue-emitting devices.

The invention relates to compounds of the formula (1)

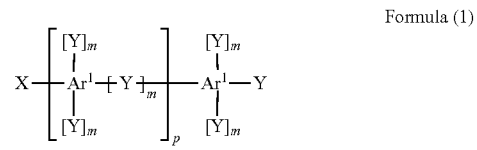

Formula (1)

where the following applies to the symbols and indices used:

$Ar^1$ is on each occurrence, identically or differently, a fused aryl or heteroaryl group having at least 14 aromatic ring atoms, which may be substituted by one or more radicals R;

X is on each occurrence, identically or differently, a group of the formula (2) or formula (3)

Formula (2)

Formula (3)

where the dashed bond denotes the link from $Ar^2$ or Q to $Ar^1$;

Y is on each occurrence, identically or differently, X, an $Ar^3$ group or an $N(Ar^3)_2$ group, where the two $Ar^3$ radicals may also be bonded to one another by a single bond or an O, S, N(R) or $C(R)_2$ group;

$Ar^2$ is on each occurrence, identically or differently, an aryl or heteroaryl group, which may be substituted by one or more radicals R and to which the group Q is bonded, with the proviso that either the group Q or a radical R other than H is bonded in the ortho-position to the $Ar^2$—$Ar^1$ bond;

$Ar^3$ is on each occurrence, identically or differently, an aromatic or heteroaromatic ring system, which may be substituted by one or more radicals R;

Q is on each occurrence, identically or differently, a linear, branched or cyclic alkylene or alkylidene group which forms two bonds to $Ar^2$ or one bond to the adjacent $Ar^1$ and one bond to $Ar^2$ and thereby forms a further ring system; Q here contains 1 to 20 C atoms and may be substituted by $R^1$, and one or more non-adjacent C atoms may also be replaced by N—$R^1$, O, S, O—CO—O, CO—O, —$CR^1$=$CR^1$— or —C≡C—, and one or more H atoms may be replaced by F, Cl, Br, I or CN;

R is on each occurrence, identically or differently, H, D, F, Cl, Br, I, CN, a straight-chain alkyl or alkoxy chain having 1 to 40 C atoms or a branched or cyclic alkyl or alkoxy group having 3 to 40 C atoms, each of which may be substituted by $R^1$ and in which one or more non-adjacent C atoms may be replaced by N—$R^1$, O, S, O—CO—O, CO—O, —CR¹=CR¹— or —C≡C— and in which one or more H atoms may be replaced by F, Cl, Br, I or CN, or an aromatic or heteroaromatic ring system having 5 to 40 aromatic ring atoms, which may also be substituted by one or more radicals $R^1$, or a combination of two, three or four of these systems; two or more radicals R here may also form a further mono- or polycyclic, aliphatic or aromatic ring system with one another;

$R^1$ is on each occurrence, identically or differently, H or a hydrocarbon radical having 1 to 20 C atoms, which may be aliphatic or aromatic or a combination of aliphatic and aromatic and in which one or more H atoms may be replaced by F;

m is on each occurrence 0 or 1;

p is on each occurrence 0, 1 or 2;

with the exception of the following compound:

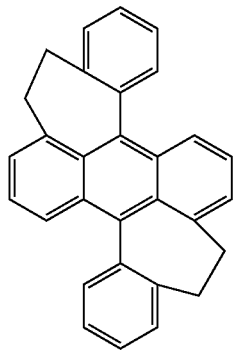

The compound of the formula (1) preferably has a glass transition temperature $T_g$ of greater than 70° C., particularly preferably greater than 100° C., very particularly preferably greater than 130° C.

For the purposes of this invention, the ortho-position is taken to mean the 1,2-position on benzene or other aromatic compounds, i.e. positions on two directly adjacent C atoms of aromatic compounds.

For the purposes of this invention, an aryl group contains 6 to 30 C atoms; for the purposes of this invention, a heteroaryl group contains 2 to 30 C atoms and at least one hetero atom, with the proviso that the total number of C atoms and hetero atoms is at least 5. The hetero atoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a fused aryl or heteroaryl group in the sense of the following definition.

For the purposes of this invention, an aromatic ring system contains 6 to 40 C atoms in the ring system. For the purposes of this invention, a heteroaromatic ring system contains 2 to 40 C atoms and at least one hetero atom in the ring system, with the proviso that the total number of C atoms and hetero atoms is at least 5. The hetero atoms are preferably selected from N, O and/or S. For the purposes of this invention, an aromatic or heteroaromatic ring system is intended to mean a system which does not necessarily contain only aryl or heteroaryl groups, but in which, in addition, a plurality of aryl or heteroaryl groups may be interrupted by a short, non-aromatic unit (less than 10% of the atoms other than H, preferably less than 5% of the atoms other than H), such as, for example, an sp³-hybridised C, N or O atom. Thus, for example, systems such as 9,9'-spiro-bifluorene, 9,9-diarylfluorene, triarylamine, diaryl ethers, etc., should also be taken to mean aromatic ring systems for the purposes of this invention. Part of the aromatic or heteroaromatic ring system here may also be a fused group in the sense of the following definition.

For the purposes of this invention, a fused aryl group is taken to mean a ring system having 10 to 40 aromatic ring atoms in which at least two aromatic rings are "fused" to one another, i.e. have at least one common edge and a common aromatic π-electron system. For the purposes of this invention, a fused heteroaryl group is taken to mean a ring system having 8 to 40 aromatic ring atoms in which at least two aromatic or heteroaromatic rings, at least one of which is heteroaromatic, are fused to one another. These ring systems may be substituted by R or unsubstituted. Examples of fused aromatic or heteroaromatic ring systems are naphthalene, quinoline, benzothiophene, anthracene, phenanthrene, phenanthroline, pyrene, perylene, chrysene, acridine, etc., while biphenyl, for example, does not represent a fused aryl group since there is no common edge between the two ring systems therein. Fluorene, for example, likewise does not represent a fused aromatic ring system since the two phenyl units therein do not form a common aromatic ring system.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methyl-butoxy. An aromatic or heteroaromatic ring system having 5-30 aromatic ring atoms, which may also in each case be substituted by the above-mentioned radicals R and which may be linked to the aromatic or hetero-aromatic system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2, 4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Depending on whether Q forms a ring system with $Ar^1$ or with $Ar^2$, the structures of the formula (4) or formula (5) thus arise for p=0 or formula (6) for p greater than or equal to 1:

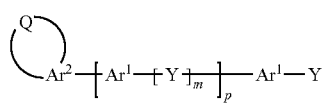

Formula (4)

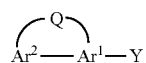

Formula (5)

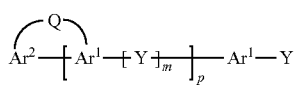

Formula (6)

The fused aryl or heteroaryl group $Ar^1$ preferably contains three, four, five or six aromatic or heteroaromatic units, which are in each case fused to one another via one or more common edges and thus form a common aromatic system and may be substituted by R or unsubstituted. The fused aryl or heteroaryl group $Ar^1$ particularly preferably contains three, four or five aromatic or heteroaromatic units, in particular three or four aromatic or heteroaromatic units, which are in each case fused to one another via one or more common edges and thus form a common aromatic system and may be substituted by R or unsubstituted. The aromatic and heteroaromatic units fused to one another are very particularly preferably selected from benzene, pyridine, pyrimidine, pyrazine and pyridazine, each of which may be substituted by R or unsubstituted, in particular benzene.

The fused aryl or heteroaryl groups $Ar^1$ are particularly preferably selected from the group consisting of anthracene, acridine, phenanthrene, phenanthroline, pyrene, naphthacene, chrysene, pentacene, phenanthroline and perylene, each of which may optionally be substituted by R. The substitution by R may be appropriate in order to obtain compounds with better solubility or in order to adjust the electronic properties. The fused aryl or heteroaryl groups $Ar^1$ are particularly preferably selected from the group consisting of anthracene, phenanthrene, pyrene or perylene, in particular anthracene and pyrene, each of which may optionally be substituted by R. The linking of the units X and Y to the anthracene preferably takes place here via the 2,6-position or via the 9,10-position, particularly preferably via the 9,10-position. The linking to the pyrene preferably takes place via the 1,6-, 1,8-, 1,3- or 2,7-position, particularly preferably via the 1,6- or 2,7-position. The linking to the phenanthrene preferably takes place via the 2,7-, 3,6-, 2,9- or 2,10-position, particularly preferably via the 2,7- or 3,6-position. The linking to the perylene preferably takes place via the 3,9-, 3,10-, 3,8- or 2,8-position, particularly preferably via the 3,9- or 3,10-position. The linking to the phenanthroline preferably takes place via the 2,9- or 3,8-position.

Particular preference is given to the following structures of the formulae (7) to (12)

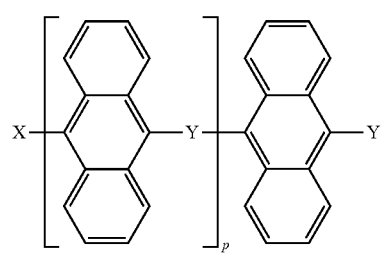

Formula (7)

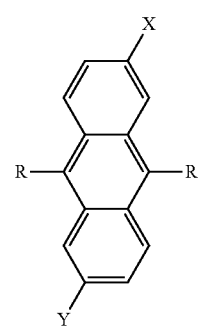

Formula (8)

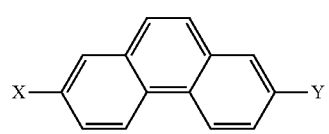

Formula (9)

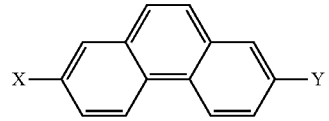

Formula (10)

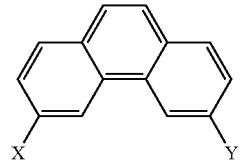

Formula (11)

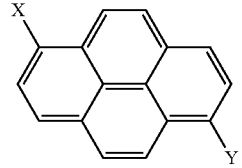

Formula (12)

where X and Y have the same meaning as described above, and where the anthracene or phenanthrene or pyrene units may be substituted by one or more radicals R.

If Y represents an $Ar^3$ group, preferred $Ar^3$ groups, identically or differently on each occurrence, are aromatic or heteroaromatic ring systems having 5 to 20 aromatic ring atoms, particularly preferably having 5 to 16 aromatic ring atoms, very particularly preferably having 6 to 14 aromatic ring atoms. The $Ar^3$ groups here may in each case be substituted by R or unsubstituted. Particular preference is given to aromatic ring systems which contain no aromatic heteroatoms. Examples of particularly preferred $Ar^3$ groups are phenyl, 1-naphthyl, 2-naphthyl, 2-phenanthrenyl, 3-phenanthrenyl, 9-anthryl, ortho-biphenyl, meta-biphenyl and para-biphenyl, each of which may be substituted by one or more radicals R.

If Y represents an N(Ar³)₂ group, Y then preferably stands for a group of the formula (13) or formula (14)

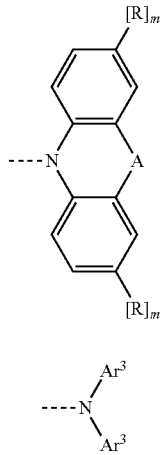

Formula (13)

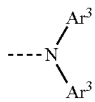

Formula (14)

where R and m have the meaning indicated above, and furthermore:

A stands for a single bond, O, S, N(R) or C(R)₂;

Ar³ is, identically or differently on each occurrence, an aryl or heteroaryl group having 5 to 20 aromatic ring atoms, which may be substituted by one or more radicals R, preferably an aryl or heteroaryl group having 6 to 14 aromatic ring atoms, which may be substituted by one or more radicals R, particularly preferably phenyl, 1-naphthyl or 2-naphthyl, each of which may be substituted by one or more radicals R.

The radicals R here are preferably H, F or an alkyl group having 1 to 4 C atoms.

Preferred Ar² groups, identically or differently on each occurrence, are aryl or heteroaryl groups having 5 to 16 aromatic ring atoms, preferably having 6 to 10 aromatic ring atoms, particularly preferably phenyl, naphthyl or anthryl, very particularly preferably phenyl.

Particularly preferred structures of the formula (2) are the following structures of the formulae (15) to (20)

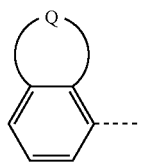

Formula (15)

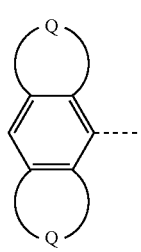

Formula (16)

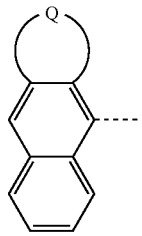

Formula (17)

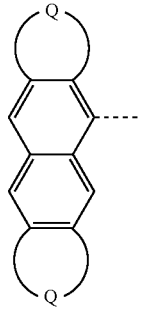

Formula (18)

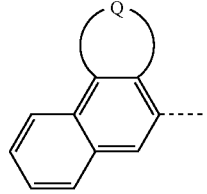

Formula (19)

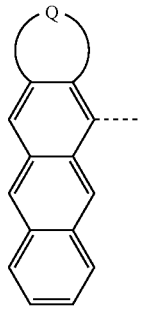

Formula (20)

where Q has the same meaning as described above, and where the phenyl or naphthyl or anthryl unit may in each case also be substituted by R; the dashed bond here denotes the link to the Ar¹ unit.

In a preferred embodiment of the invention, the groups X and Y are selected to be identical.

In a further preferred embodiment of the invention, the groups X and Y are selected to be different, and Y stands for a fused aryl or heteroaryl group having 9 to 20 aromatic ring atoms or for an N(Ar³)₂ group.

Q is preferably a linear alkylene chain having 2 to 15 C atoms or a branched or cyclic alkylene group having 3 to 15 C atoms, each of which may be substituted by $R^1$ and in which one or more non-adjacent C atoms may also be replaced by N—$R^1$, O or S and one or more H atoms may be replaced by F or CN. Q is particularly preferably a linear, branched or cyclic alkylene chain having 3 to 10 C atoms, which may be substituted by $R^1$ and in which one or more non-adjacent C atoms may be replaced by N—$R^1$ or O and one or more H atoms may be replaced by F.

Q is preferably bonded to the ortho-position of Ar², where the ortho-position relates to the linking of Ar² to Ar¹.

The preferred ring size formed by Q depends on whether the further ring system is formed with Ar¹ or with Ar². If Q forms a ring system with Ar¹, the ring size of the ring system formed by Ar¹, Ar² and Q is preferably a 6-membered ring, a 7-membered ring or an 8-membered ring, particularly preferably a 7-membered ring or an 8-membered ring. These relatively large ring systems are preferred since the Ar² group is thereby rotated with respect to Ar¹ and thus results in dark-blue absorption and emission. If Q forms a ring system with Ar², the ring system formed by Ar² and Q preferably contains 3 to 8 ring atoms; it particularly preferably contains 4, 5, 6 or 7 ring atoms, very particularly preferably 5, 6 or 7 ring atoms.

Q preferably forms a ring system with Ar². In this case, the two links of Q to Ar² may take place in different positions of Ar², for example in the 1,2-position (ortho), in the 1,3-position (meta) or in the 1,4-position (para). The two links of Q to Ar² preferably take place in the ortho-position to one another.

In a particularly preferred embodiment of the invention, Q is selected in such a way that it either contains no benzylic protons, i.e. no protons on the C atom linked directly to Ar², or that a bridgehead C atom is linked directly to Ar². This preference is due to the higher reactivity of benzylic protons, which may result in undesired side reactions in the OLED. Benzylic protons can be avoided by introducing substituents into the corresponding positions or by using branched alkylene chains for Q. Benzylic protons can furthermore be avoided by not directly bonding a carbon atom, but instead, for example, an oxygen atom to Ar². The preference of bridgehead C atoms in the direct link to Ar² is due to the fact that protons optionally bonded to the bridgehead have very low reactivity and therefore do not have the above-mentioned disadvantages.

Very particularly preferred groups of the formula (2) are the groups of the formulae (21) to (24) shown below Formula (21)

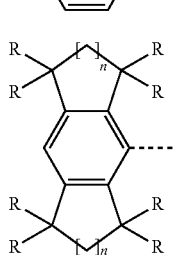

Formula (22)

Formula (23)

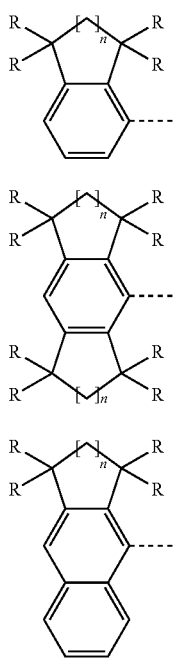

Formula (24)

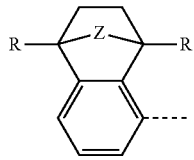

where R has the same meaning as described above, and furthermore:

Z is $CR_2$, O, S, NR, PR, P(=O)R, $SiR_2$ or $CR_2$—$CR_2$;

n is 1, 2 or 3, preferably 2;

the dashed bond here denotes the link to the Ar¹ unit.

Preferred structures of the formulae (21) to (23) are those in which the radical R stands for a group other than H or D.

Preference is furthermore given to compounds of the formula (1) in which the index p is equal to 0 or 1; the index p is particularly preferably equal to 0.

Some compounds of the formula (1) can form atropisomers, i.e. isomers which arise due to hindered rotation about the X—Ar¹ and about the Ar¹—Y bond. If the compounds of the formula (1) form atropisomers, the invention encompasses mixtures both of the two (or where appropriate also more) different atropisomers and the enriched or pure atropisomers of the compound.

Examples of suitable compounds of the formula (1) are the structures (1) to (98) shown below.

(1)

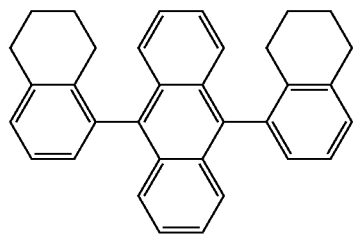

(2)

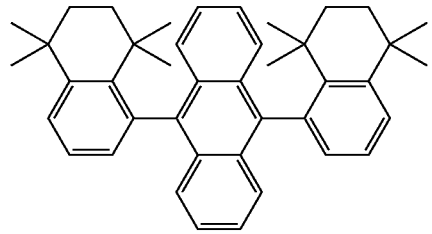

(3)

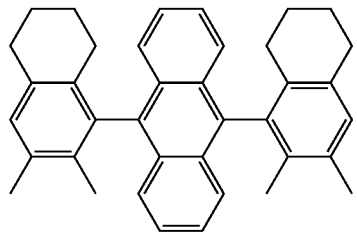

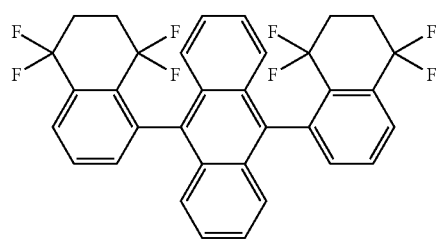 (4)
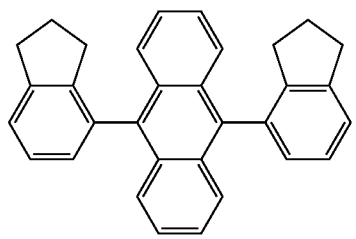 (5)
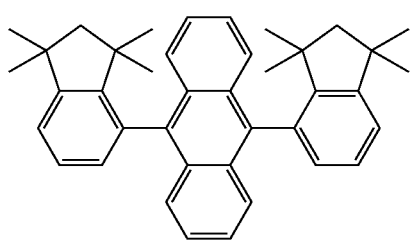 (6)
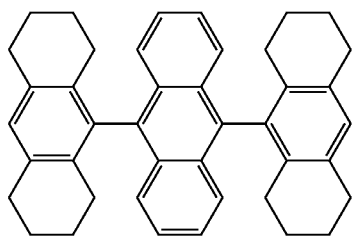 (7)
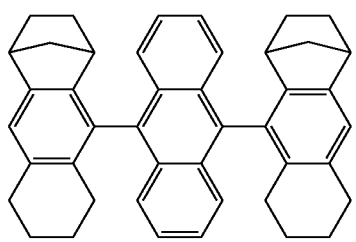 (8)
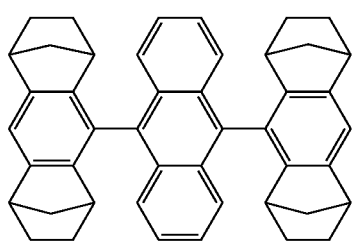 (9)
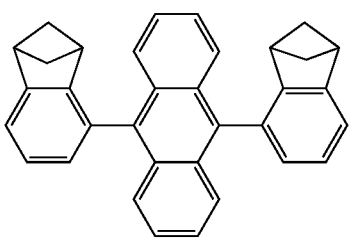 (10)
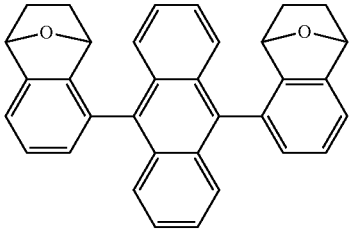 (11)
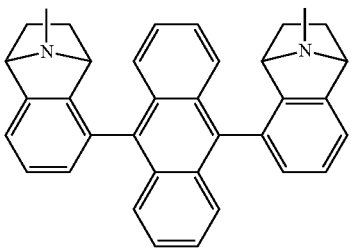 (12)
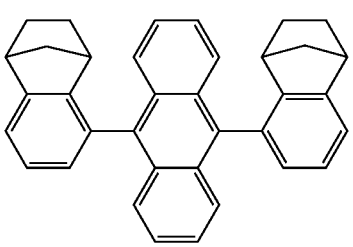 (13)
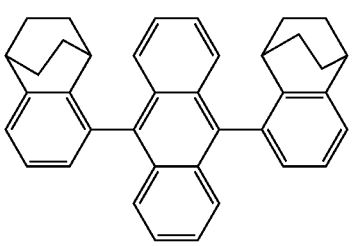 (14)
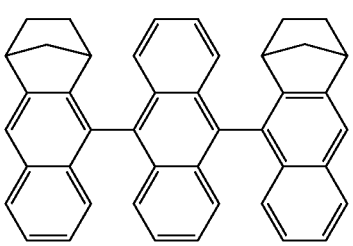 (15)

-continued
(16)
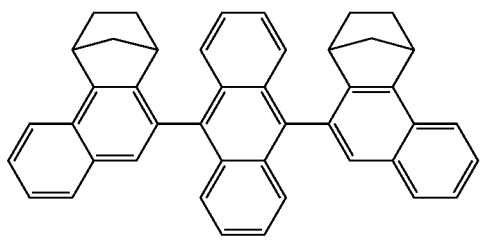
(17)
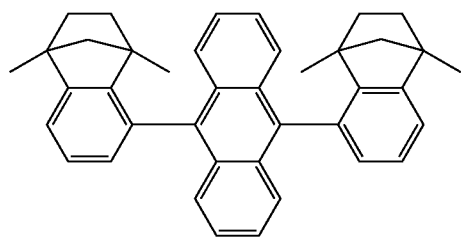
(18)
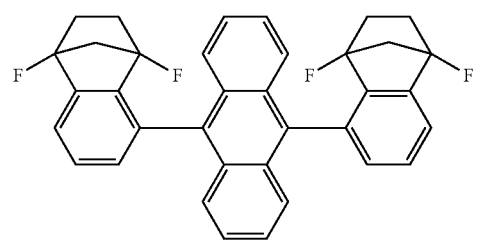
(19)
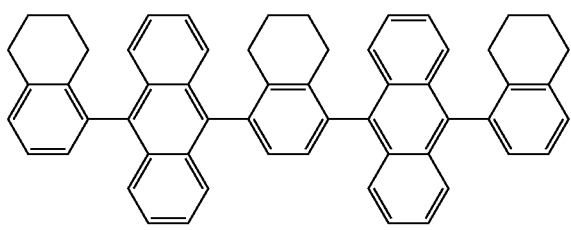
(20)
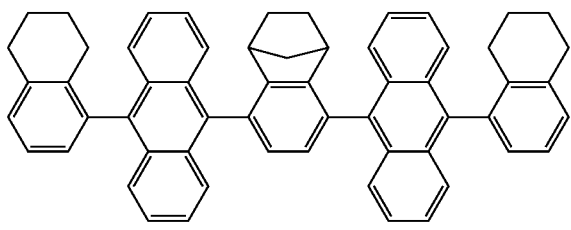
(21)
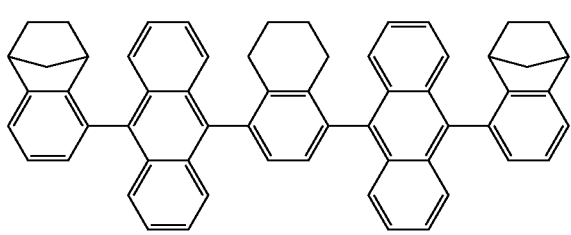
-continued
(22)
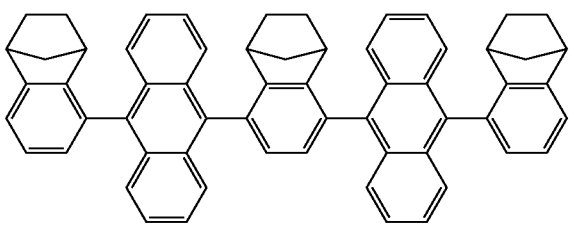
(23)
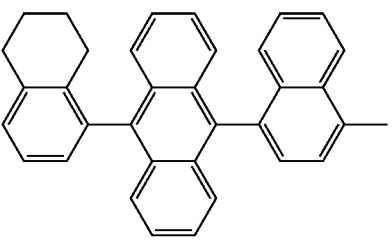
(24)
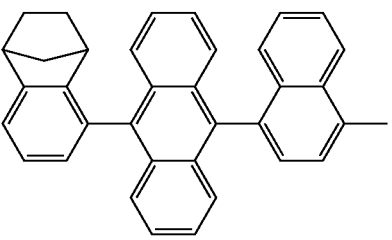
(25)
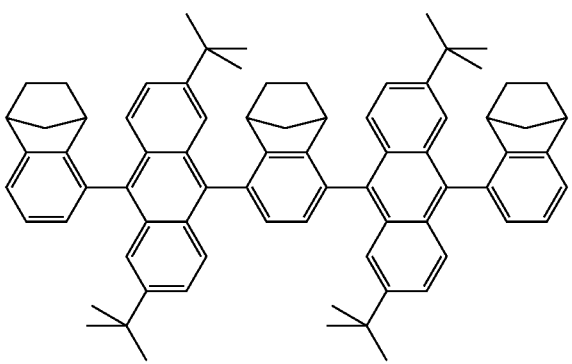
(26)
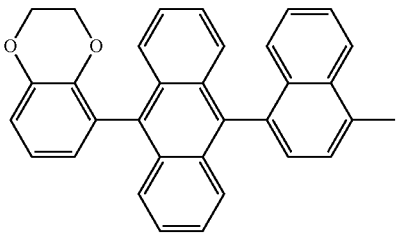
(27)
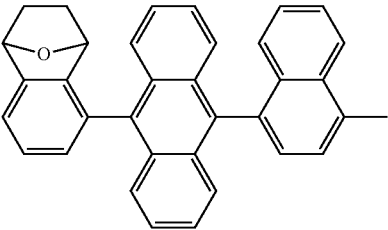

(28)
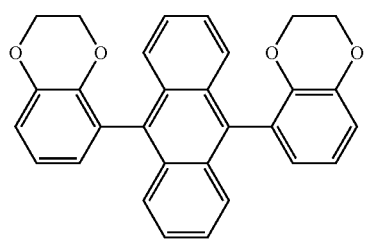
(29)
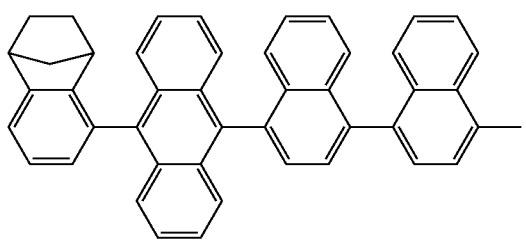
(30)
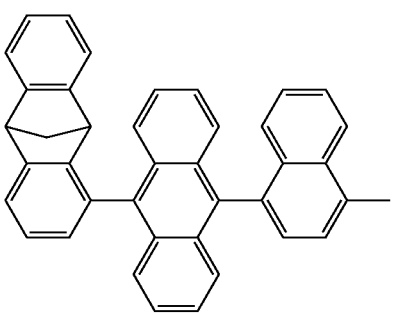
(31)
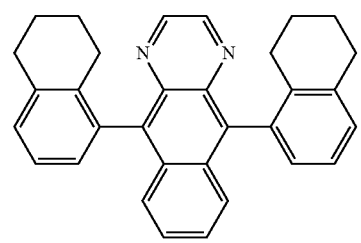
(32)
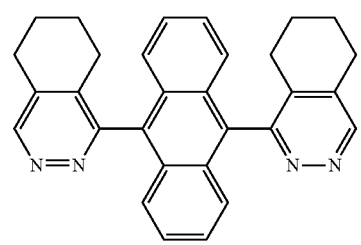
(33)
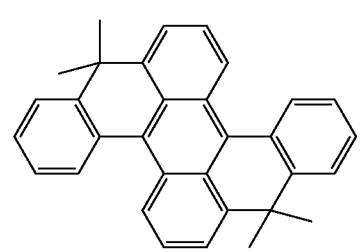
(34)
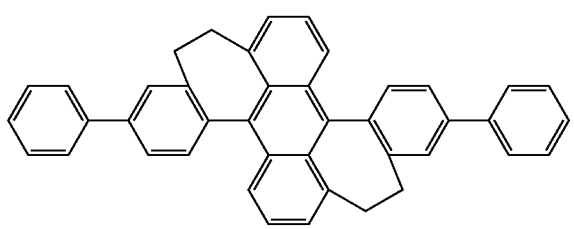
(35)
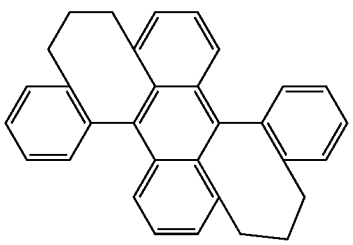
(36)
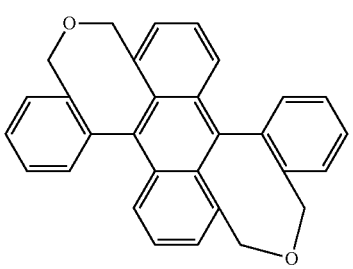
(37)
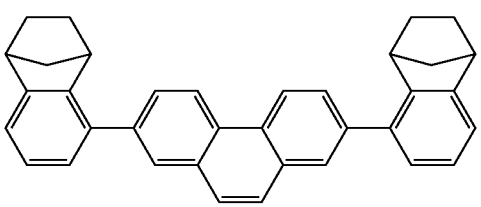
(38)
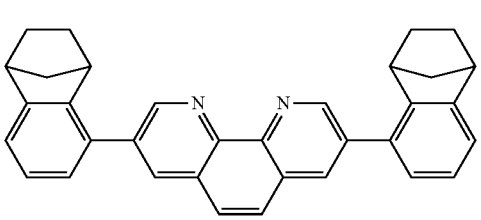
(39)
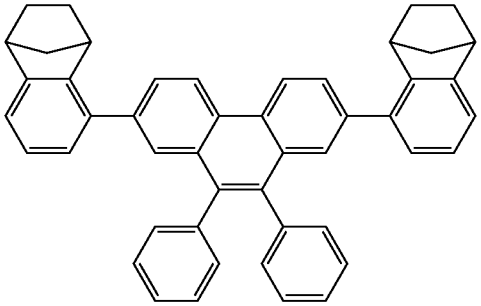

(40)
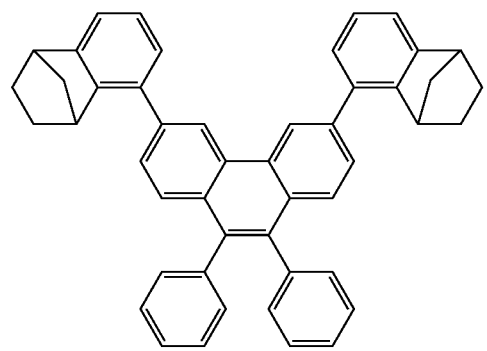
(41)
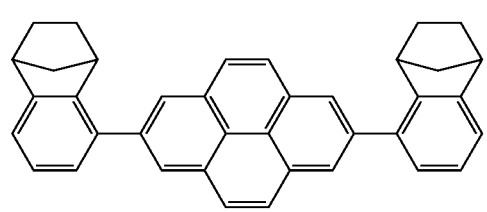
(42)
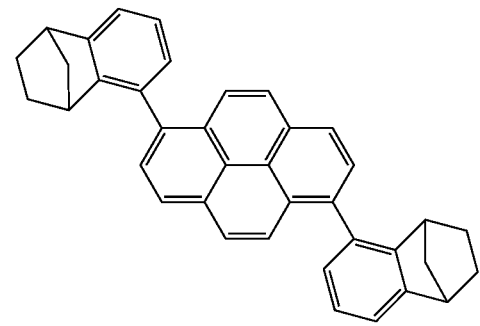
(43)
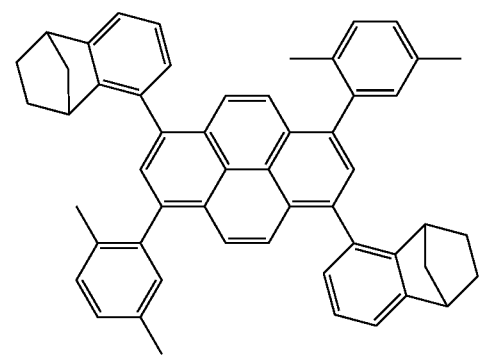
(44)
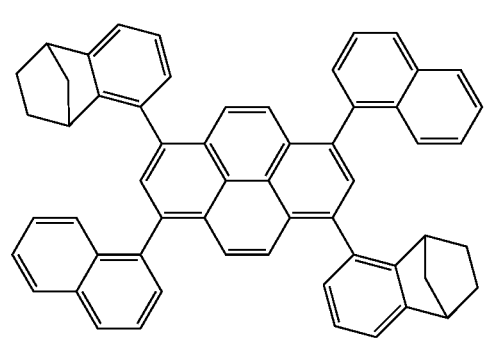
(45)
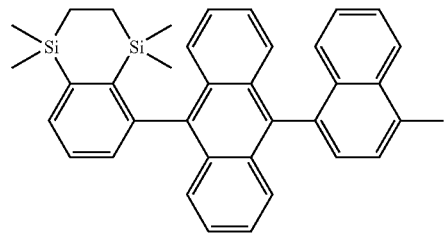
(46)
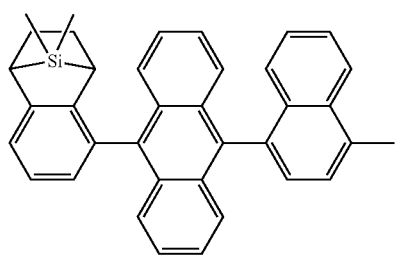
(47)
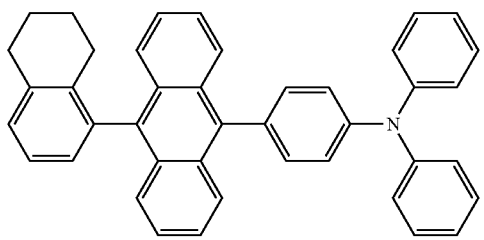
(48)
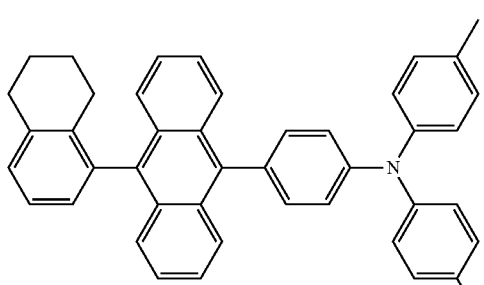
(49)
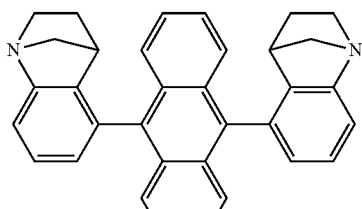
(50)
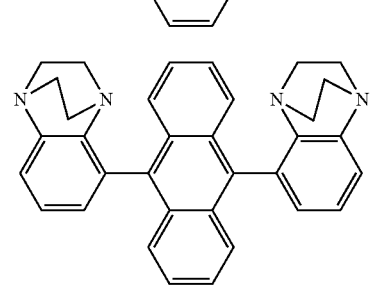

-continued
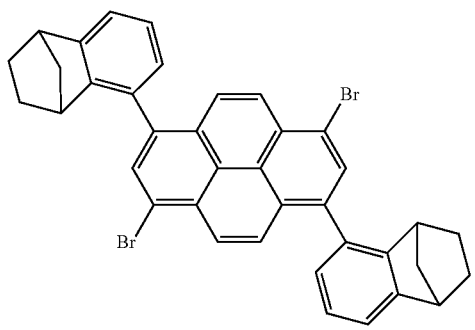
(51)
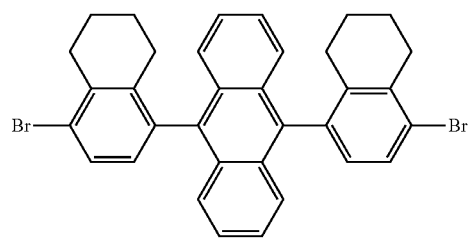
(52)
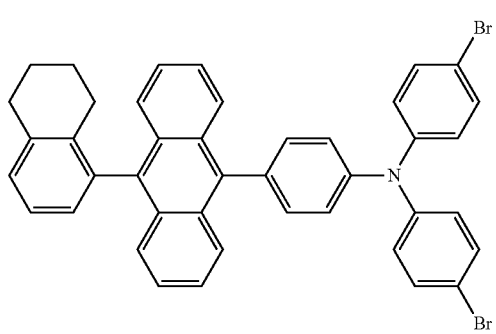
(53)
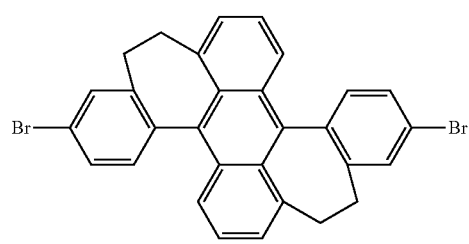
(54)
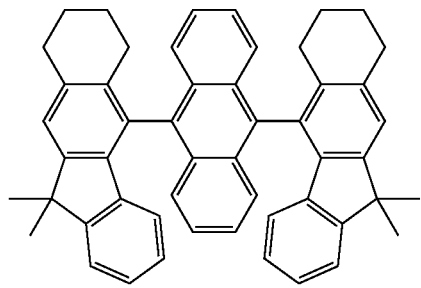
(55)
-continued
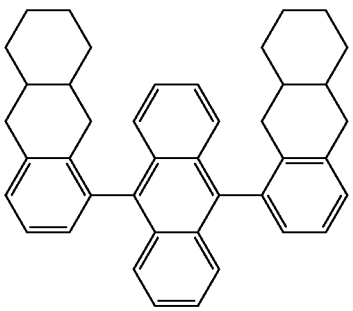
(56)
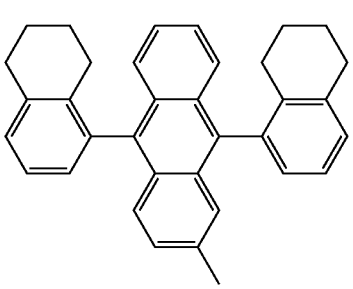
(57)
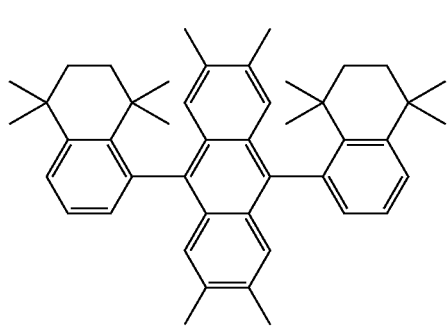
(58)
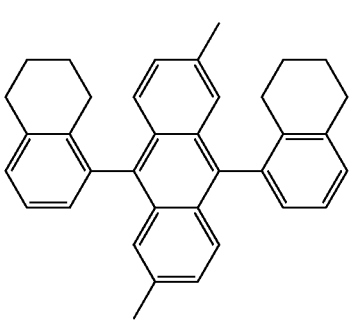
(59)
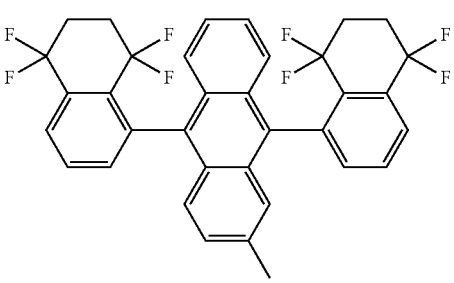
(60)

(61) 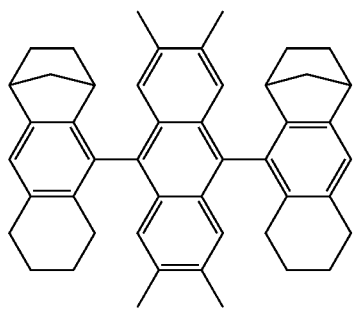
(62) 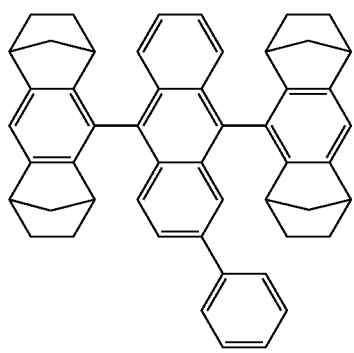
(63) 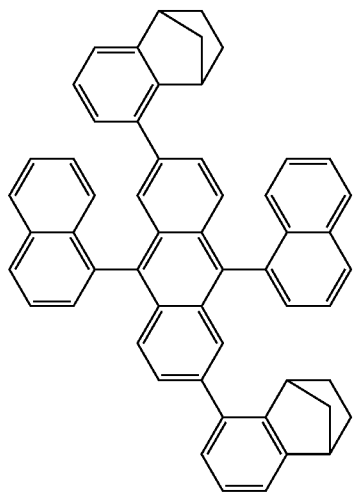
(64) 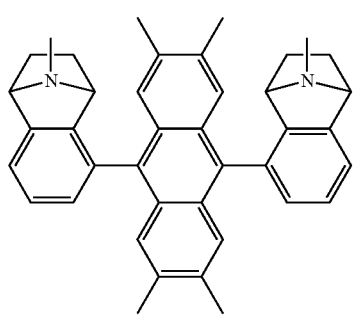
(65) 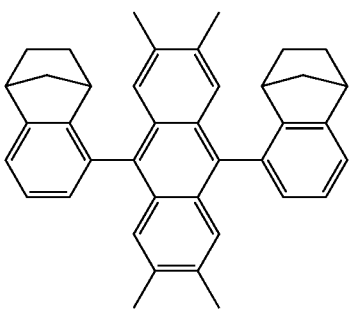
(66) 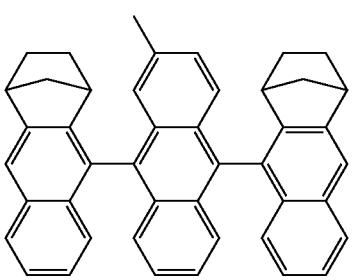
(67) 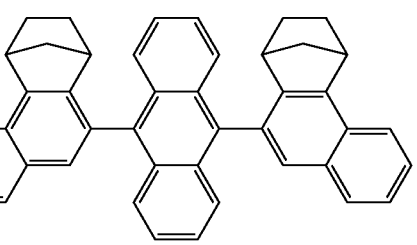
(68) 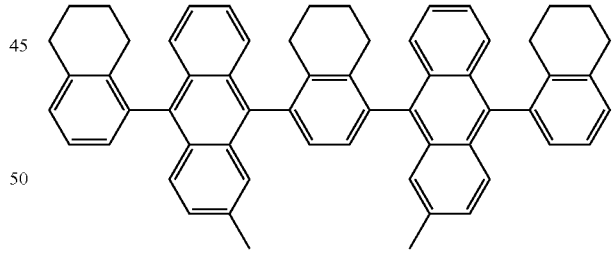
(69) 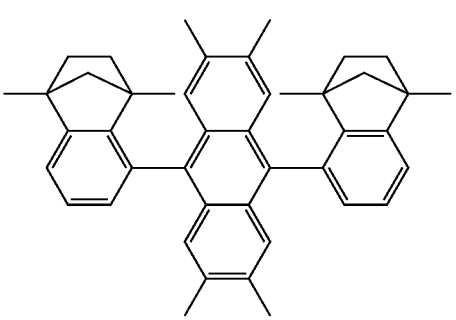

(70) 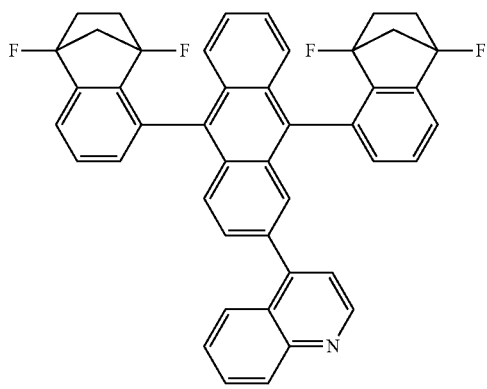
(74) 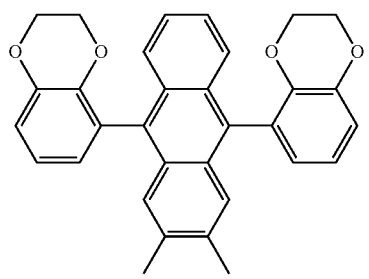
(71) 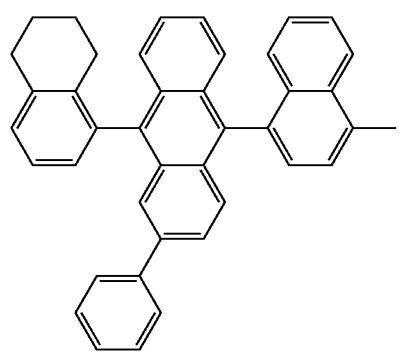
(75) 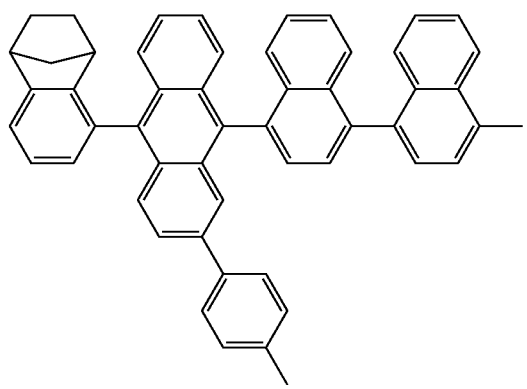
(72) 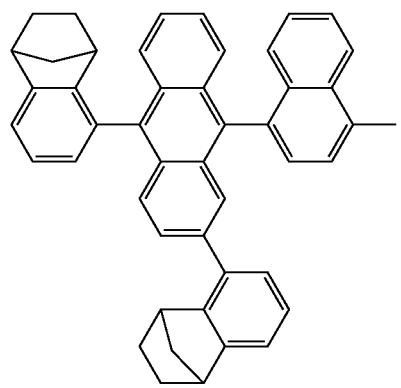
(76) 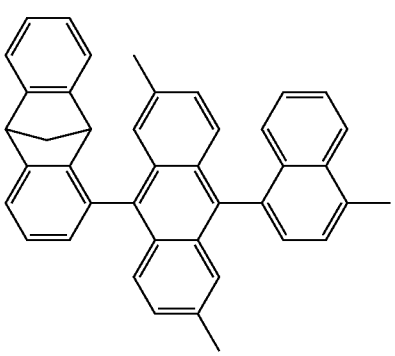
(73) 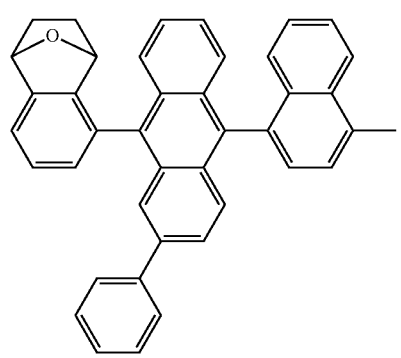
(77) 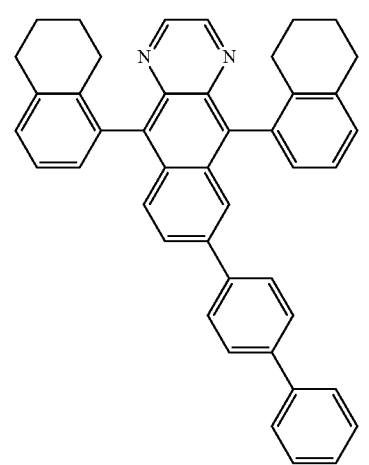

(78)
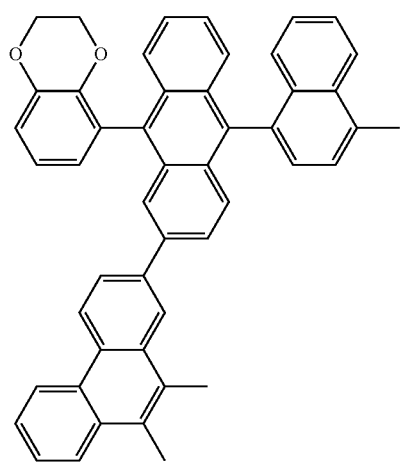
(79)
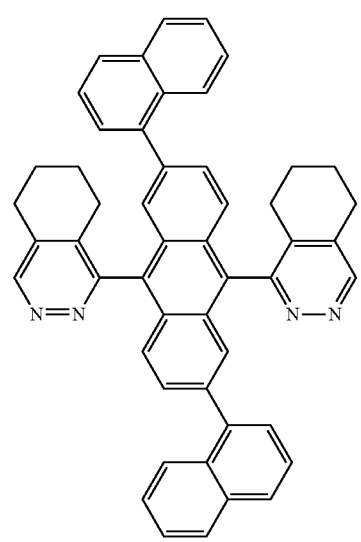
(80)
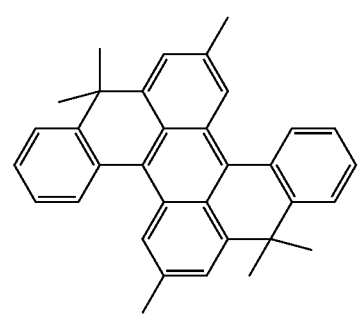
(81)
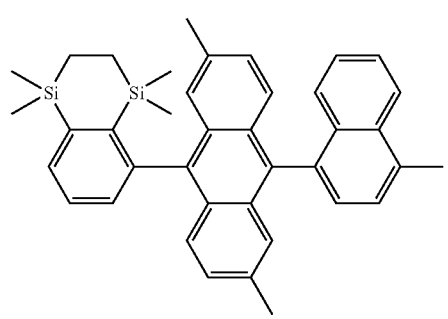
(82)
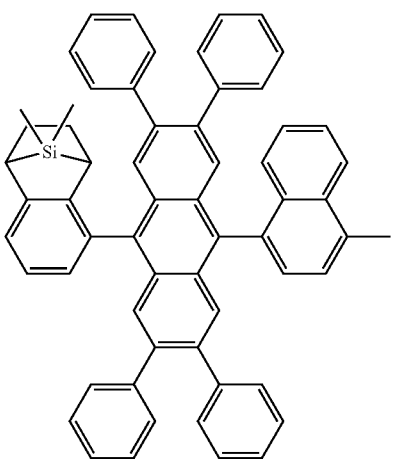
(83)
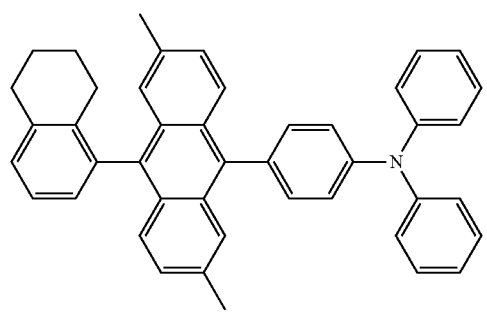
(84)
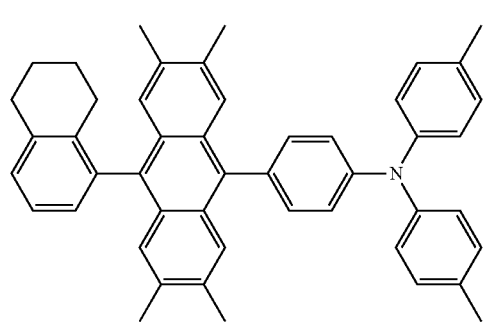
(85)
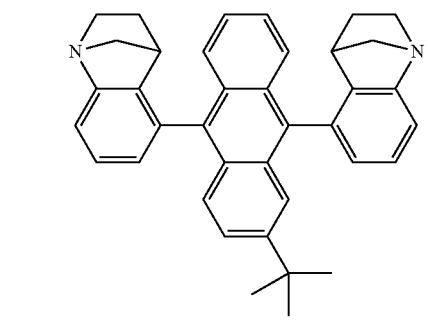

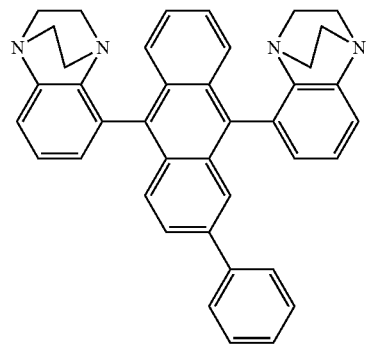
(86)
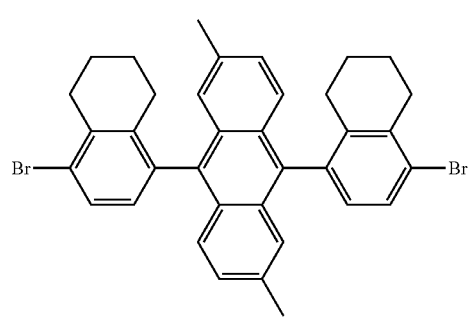
(87)
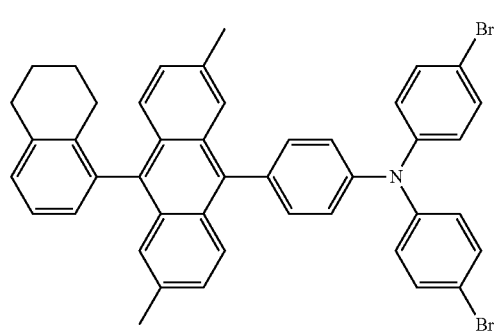
(88)
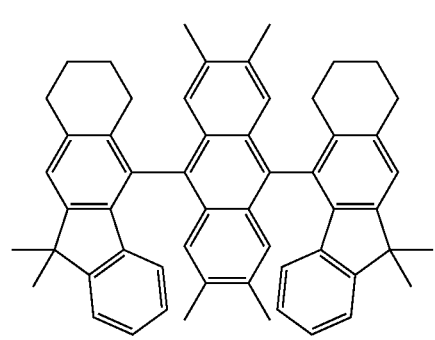
(89)
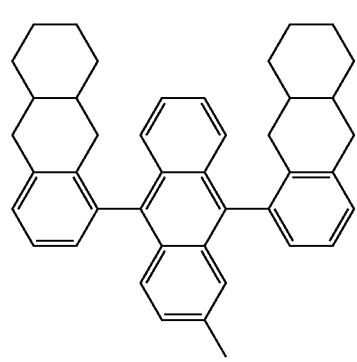
(90)
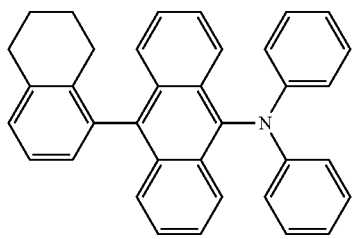
(91)
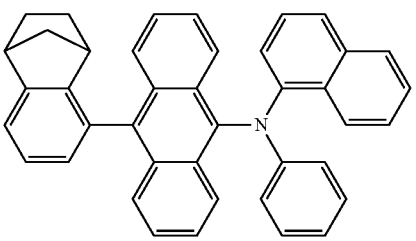
(92)
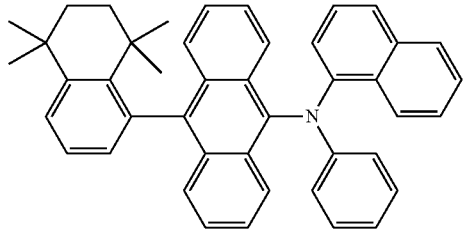
(93)
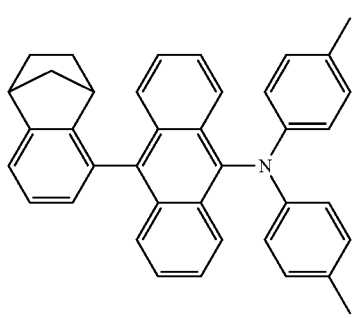
(94)
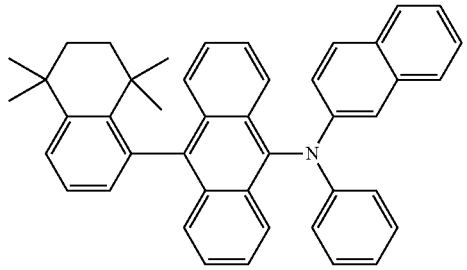
(95)
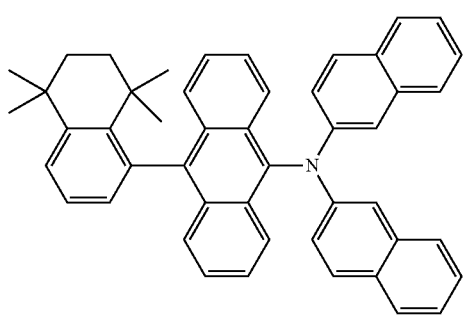
(96)

(97)

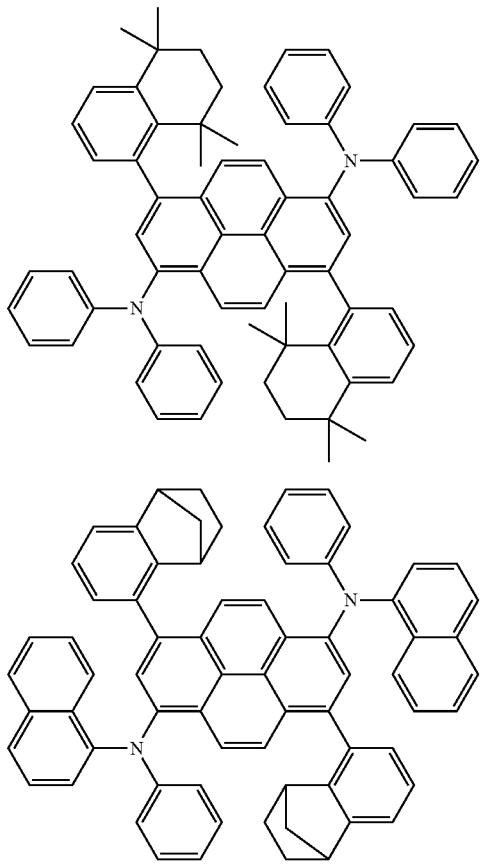

(98)

Compounds of the formula (1) can be synthesised by standard methods of organic chemistry. A standard method which is used for the preparation of similar systems in accordance with the prior art and which can also be used for the synthesis of the compounds according to the invention is the Suzuki coupling between an aromatic halide and an aromatic boronic acid derivative. Thus, for example, the Suzuki coupling of a boronic acid derivative of group X to a dihalide of a fused aromatic group Ar¹ gives symmetrically substituted compounds of the formula (1). Asymmetrically substituted compounds of the formula (1) can be synthesised by, for example, firstly carrying out the coupling between X and Ar¹, then halogenating Ar¹ and coupling the product to a boronic acid derivative of Y. It is equally possible firstly to carry out the coupling between Ar¹ and Y, then to halogenate Ar¹ and to couple the product to a boronic acid derivative of X. Other coupling reactions are likewise possible, for example Stille, Negishi, Sonogashira and Heck coupling, Grignard cross-coupling, etc. The starting compound X in the form of the halide can be prepared, inter alia, by direct bromination of the corresponding cycloalkylaromatic compounds, such as, for example, 1,2,3,4-tetrahydronaphthalene, to give 5-bromo-1,2,3,4-tetrahydronaphthalene (Ranu et al., *Synthetic Communications* 1992, 22(8), 1095) or of indane to give 4-bromo-2,3-dihydro-1H-indane (Kostermans et al., *J. Org. Chem.* 1988, 53(19), 4531) or also by cycloadditions from intermediate arynes, as, for example, in the case of 5-bromo-1,4-methano-1,2,3,4-tetrahydronaphthalene, which can be obtained from 1,3-dibromo-2-fluorobenzene and cyclopentadiene (Tanida et al., *J. Am. Chem. Soc.* 1956, 87(21), 4794). The aryne can be prepared in situ by methods known to the person skilled in the art of organic synthesis. A further method for the preparation of the aryne in situ consists in the conversion of a corresponding ortho-halophenol ino the corresponding triflate, which can then be reacted with magnesium to give the aryne and scavenged using a diene.

Some general access routes to the classes of compound according to the invention are shown in the following schemes:

Preparation of the Substituents X

Tetrahydronaphth-1-yls

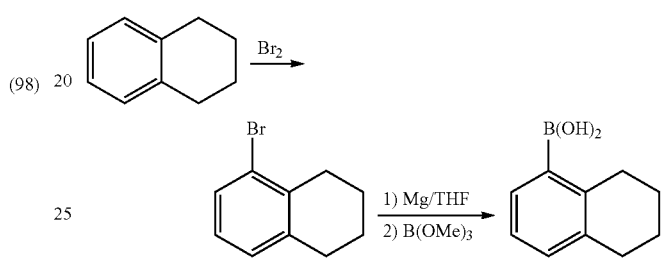

1,4-Methano-1,2,3,4-tetrahydronaphth-1-yls

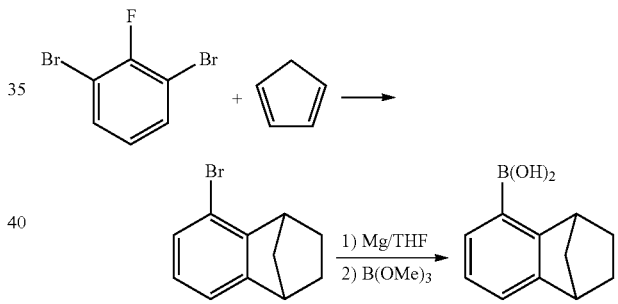

Coupling to Give Structures (1), (13) and (42) Shown Above:

Structure (1):

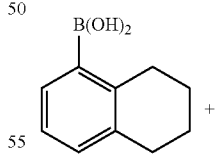

+

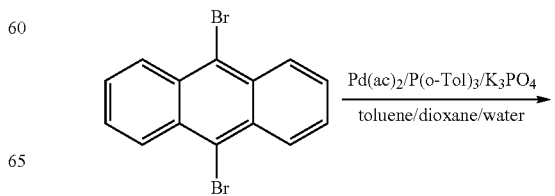

-continued

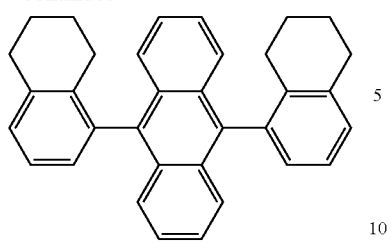

Structure (13):

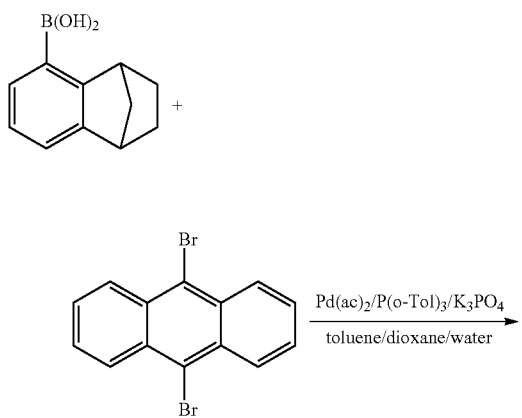

Structure (42):

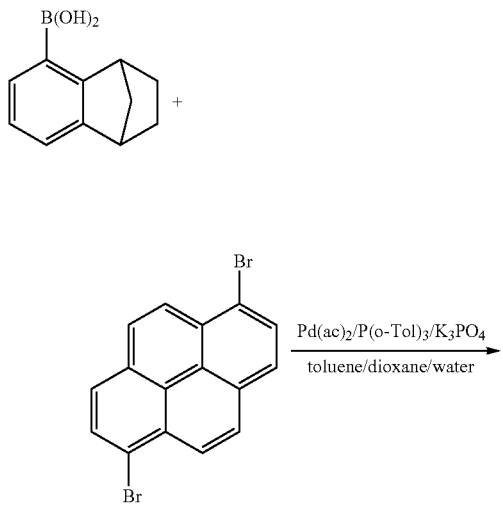

-continued

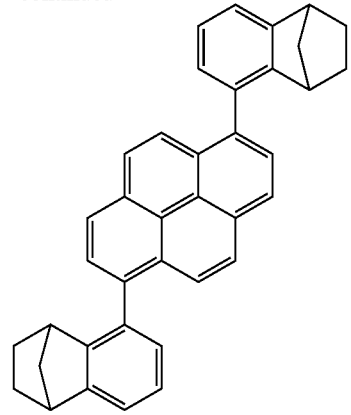

If the compounds of the formula (1) are able to form atropisomers, it may be sensible to separate the atropisomers in order to have available pure compounds for use in organic electronic devices. The way in which atropisomers can be separated is described in detail, for example, in the unpublished application EP 04026402.0. For example, recrystallisation, chromatography or fractional sublimation are suitable for this purpose.

Suitably functionalised compounds of the formula (1), in particular brominated compounds, such as, for example, the structures (51) to (56), (87) and (88) shown above, can also be used for incorporation into polymers.

The invention therefore furthermore relates to conjugated, partially conjugated or non-conjugated polymers, oligomers or dendrimers comprising recurring units of the formula (1). At least one radical R here on units of the formula (1) represents a bond to the polymer. As further recurring units, the polymers comprise, for example, fluorenes (for example in accordance with EP 842208 or WO 00/22026), spirobifluorenes (for example in accordance with EP 707020, EP 894107, WO 03/020790 or EP 04028865.6), para-phenylenes (for example in accordance with WO 92/18552), dihydrophenanthrenes (for example in accordance with WO 05/014689), phenanthrenes (for example in accordance with WO 05/104264), indenofluorenes (for example in accordance with WO 04/041901 or WO 04/113412), carbazoles (for example in accordance with WO 04/070772 or WO 04/113468), anthracenes, naphthalenes (for example in accordance with EP 04030093.1), triarylamines, metal complexes or thiophenes (for example in accordance with EP 1028136) or also a plurality of these units. Homopolymers of the recurring units of the formula (1) are also possible.

The invention furthermore relates to mixtures comprising at least one compound of the formula (1) and one or more dopants. The dopants are preferably selected from the class of aromatic anthracenamines, aromatic anthracenediamines, aromatic pyrenamines, aromatic pyrenediamines, monostyrylamines, distyrylamines, tristyrylamines, tetrastyrylamines, styrylphosphines, styryl ethers and arylamines. An aromatic anthracenamine is taken to mean a compound in which a diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines and pyrenediamines are defined analogously. A monostyrylamine is taken to mean a compound which contains one styryl group and at least one, preferably aromatic, amine. A distyrylamine is taken to mean a compound which contains two styryl groups and at least one, preferably aromatic, amine. A tristyrylamine is taken to mean a compound which contains three styryl groups and at least one, preferably aromatic, amine. A tetrastyrylamine is taken to mean a compound which contains four styryl groups and at least one, preferably aromatic, amine. Corresponding phosphines and ethers are defined analogously to the amines. For the purposes of this invention, an arylamine or an aromatic amine is taken to mean a compound which contains three aromatic or heteroaromatic ring systems bonded directly to the nitrogen. The styryl groups are particularly preferably stilbenes, which may also be further substituted. Preferred dopants are selected from the classes of the tristilbenamines, the aromatic stilbenediamines, the anthracenediamines and the pyrenediamines. Particularly preferred dopants are selected from the class of the tristyrylamines and the stilbenediamines. Examples of such dopants are substituted or unsubstituted tristilbenamines or the dopants described in WO 06/000388 and in the unpublished patent applications EP 04028407.7 and EP 05001891.0.

The invention furthermore relates to the use of compounds of the formula (1) or corresponding polymers in organic electronic devices.

The present invention furthermore relates to organic electronic devices comprising anode, cathode and at least one organic layer which comprises at least one compound of the formula (1) or a corresponding polymer.

The organic electronic device is preferably selected from the group of electronic devices consisting of organic and polymeric light-emitting diodes (OLEDs, PLEDs), organic field-effect transistors (O-FETs), organic thinfilm transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors and organic laser diodes (O-lasers). Preference is given to organic and polymeric light-emitting diodes.

The organic electronic device comprises one or more organic layers, of which at least one layer comprises at least one compound of the formula (1). If it is an organic electroluminescent device, at least one organic layer is an emission layer. In organic transistors, at least one organic layer is a charge-transport layer. In organic electroluminescent devices, further layers may also be present in addition to the emitting layer. These can be, for example: hole-injection layer, hole-transport layer, charge-blocking layer, electron-transport layer and/or electron-injection layer. However, it should be pointed out at this point that each of these layers does not necessarily have to be present.

The compounds of the formula (1) can be used as host material for dopants which emit light from the singlet state or from a state of higher spin multiplicity (for example the triplet state), as dopant, as hole-transport material, as electron-transport material or as hole-blocking material. The preferred use of compounds of the formula (1) depends on the substituents present, in particular on the group Y.

If the group Y stands for a group X or for an aromatic or heteroaromatic ring system, in particular for a fused aryl group, the compound of the formula (1) is preferably used as host material together with a dopant which emits light from the singlet state. These compounds are also suitable for use in an electron-transport layer and/or in a hole-blocking layer. Preferred dopants are selected from the group of aromatic anthracenamines, aromatic anthracenediamines, aromatic pyrenamines, aromatic pyrenediamines, monostyrylamines, distyrylamines, tristyrylamines, tetrastyrylamines, styrylphosphines, styryl ethers and arylamines, where these classes of compound are as defined above.

If the group Y stands for an $N(Ar^3)_2$ group, the compound of the formula (1) is preferably employed as emitting compound (emitting dopant). It is then preferably employed in combination with a host material. Suitable as host material are, for example, the above-mentioned compounds according to the invention, but also other host materials as usually used in accordance with the prior art. These are, in particular, oligoarylenes (for example 2,2',7,7'-tetraphenyl-spirobifluorene in accordance with EP 676461 or dinaphthylanthracene), in particular oligoarylenes containing fused aromatic groups, oligoarylenevinylenes (for example DPVBi or spiro-DPVBi in accordance with EP 676461), polypodal metal complexes (for example in accordance with WO 04/081017), hole-conducting compounds (for example in accordance with WO 04/058911), electron-conducting compounds, in particular ketones, phosphine oxides, sulfoxides, etc. (for example in accordance with WO 05/084081 or WO 05/084082), atropisomers (for example in accordance with the unpublished application EP 04026402.0) or boronic acid derivatives (for example in accordance with the unpublished application EP 05009643.7). Particularly preferred host materials are selected from the classes of oligoarylenes containing naphthalene, anthracene and/or pyrene or atropisomers of these compounds, oligoarylenevinylenes, ketones, phosphine oxides and sulfoxides. Very particularly preferred host materials are selected from the classes of oligoarylenes containing anthracene and/or pyrene or atropisomers of these compounds, phosphine oxides and sulfoxides.

The proportion of the dopant in the mixture of the emitting layer is between 0.1 and 99.0% by weight, preferably between 0.5 and 50.0% by weight, particularly preferably between 1.0 and 20.0% by weight, in particular between 1.0 and 10.0% by weight. Correspondingly, the proportion of the host material in the emitting layer is between 1.0 and 99.9% by weight, preferably between 50.0 and 99.5% by weight, particularly preferably between 80.0 and 99.0% by weight, in particular between 90.0 and 99.0% by weight.

If the group Y stands for an $N(Ar^3)_2$ group, the compound of the formula (1) can also be employed as hole-transport compound. It is then preferably employed in a hole-transport layer or in a hole-injection layer. For the purposes of this invention, a hole-injection layer is a layer which is directly adjacent to the anode. For the purposes of this invention, a hole-transport layer is a layer which is between a hole-injection layer or also another hole-transport layer and an emitting layer.

Preference is furthermore given to an organic electronic device which is characterised in that one or more layers are coated by a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electronic device which is characterised in that one or more layers are coated by the OVPD (organic vapour phase deposition) process or with the aid of carrier-gas sublimation, in which the materials are generally applied at a pressure between $10^{-5}$ mbar and 1 bar.

Preference is furthermore given to an organic electronic device which is characterised in that one or more layers are produced from solution, such as, for example, by spin coating, or by any desired printing process, such as, for example, screen printing, flexographic printing or offset printing, but particularly preferably LITI (light induced thermal imaging, thermal transfer printing) or ink-jet printing.

The emitting devices described above have the following surprising advantages over the prior art:
1. The stability of corresponding devices is greater compared with systems in accordance with the prior art, which is particularly evident from a longer lifetime.
2. In contrast to compounds used to date, which were in some cases very difficult to purify due to their poor solubility, the compounds of the formula (1) are readily soluble and therefore easier to purify and also easier to process from solution.
3. In contrast to compounds used to date which have no substituents on X in the ortho-position to the link to Ar$^1$, the compounds of the formula (1) according to the invention can also be employed as host materials for dark-blue emitters, while similar materials in accordance with the prior art, such as, for example, in accordance with JP 2005/008600, are only suitable for pale-blue emitters.
4. The use of the compounds according to the invention in OLEDs results in greater efficiency of the light emission.

The invention is explained in greater detail by the following examples, without wishing to be restricted thereby.

EXAMPLES

The following syntheses are carried out under a protective-gas atmosphere, unless indicated otherwise. The starting materials can be purchased from ALDRICH or ABCR (tris(dibenzylideneacetone)dipalladium(0), 2-dicyclohexylphosphino-2,6-dimethoxybiphenyl, 9,10-dibromoanthracene, 1,6-dibromopyrene, 1,3,6,8-tetrabromopyrene, inorganics, solvents). 5-Bromo-1,2,3,4-tetrahydro-1,4-methanonaphthalene is prepared by the method of Tanida et al., *J. Am. Chem. Soc.* 1965, 87(21), 4794, and 5-bromo-1,1,4,4-tetramethyl-1,2,3,4-tetrahydro-8-methylnaphthalene is prepared analogously to 6-bromo-1,1,4,4-tetramethyl-1,2,3,4-tetrahydronaphthalene by the method of Garipova at al., *Tetrahedron* 2005, 61(20), 4755. 5-Bromo-1,2,3,4-tetrahydronaphthalene is synthesised as described in *Synthetic Communications* 1992, 22(8), 1095-1099. (5,6,7,8-Tetrahydro-1-naphthyl)boronic acid is synthesised as described in US 2002/019527.

Example 1

9,10-Bis(1,2,3,4-tetrahydro-1,4-methanonaphth-5-yl)anthracene a) 1,2,3,4-Tetrahydro-1,4-methanonaphthalene-5-boronic acid

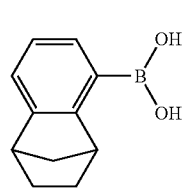

100 ml (250 mmol) of n-butyllithium (2.5M in hexane) are added dropwise to a solution, cooled to −78° C., of 44.6 g (200 mmol) of 5-bromo-1,2,3,4-tetrahydro-1,4-methanonaphthalene in 500 ml of THF. The reaction mixture is stirred at −78° C. for 1 h, and a mixture of 33.5 ml (300 mmol) of trimethyl borate in 50 ml of THF is then added rapidly. After warming to −10° C., the mixture is hydrolysed using 10 ml of 2.5M hydrochloric acid, and 500 ml of methyl tert-butyl ether are then added. The organic phase is separated off, washed with water, dried over sodium sulfate and evaporated to dryness. The residue is taken up in 200 ml of n-heptane, and the colourless solid is filtered off with suction, washed with n-heptane and dried under reduced pressure. Yield: 24.1 g (128 mmol), 64.1% of theory; purity: 98% according to $^1$H-NMR.

b) 9,10-Bis(1,2,3,4-tetrahydro-1,4-methanonaphth-5-yl)anthracene

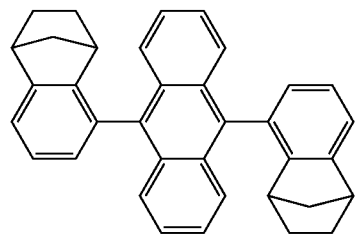 [SMILES: c1cc(-c2c3ccccc3c(-c3cccc4c3C3CCC4C3)c3ccccc23)c2c(c1)C1CCC2C1]

915 mg (1 mmol) of tris(dibenzylideneacetone)dipalladium(0) and 821 mg (2 mmol) of 2-dicyclohexylphosphino-2,6-dimethoxybiphenyl are added to a suspension of 16.8 g (50 mmol) of 9,10-dibromoanthracene, 21.6 g (115 mol) of 1,2,3,4-tetrahydro-1,4-methanonaphthalene-5-boronic acid and 66.9 g (315 mmol) of tripotassium phosphate in 400 ml of anhydrous toluene, and the mixture is refluxed for 16 h. After the reaction mixture has been cooled, 400 ml of water are added, and the precipitate is filtered off with suction, washed three times with 200 ml of water each time, washed three times with 200 ml of ethanol each time, dried under reduced pressure and subsequently chromatographed on silica gel (eluent heptane/toluene 8:2, v/v, column temperature 50° C.). Sublimation: p=1×10$^{-5}$ mbar, 300° C. Yield: 13.1 g (28 mmol), 56.6% of theory; purity: 99.5% according to $^1$H-NMR (including all isomers).

Example 2

1,6-Bis(1,2,3,4-tetrahydro-1,4-methanonaphth-5-yl)pyrene

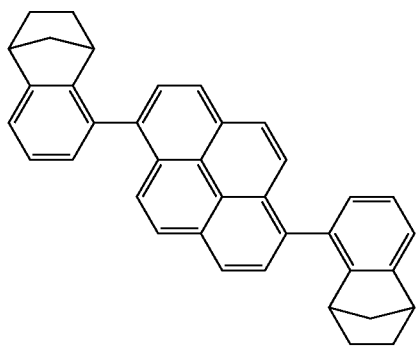 [SMILES: c1cc(-c2ccc3ccc4c(-c5cccc6c5C5CCC6C5)ccc5ccc2c3c54)c2c(c1)C1CCC2C1]

Preparation analogous to Example 1. Instead of 9,10-dibromoanthracene, 18.0 g (50 mmol) of 1,6-dibromopyrene are used. Purification by recrystallisation from NMP. Yield: 16.8 g (34.5 mmol), 69.0% of theory; purity: 99.9% according to $^1$H-NMR.

Example 3

9,10-Bis(5,6,7,8-tetrahydro-1-naphthyl)anthracene

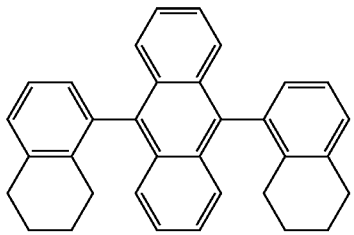 [SMILES: c1cc2c(c(-c3c4ccccc4c(-c4cccc5c4CCCC5)c4ccccc34)c1)CCCC2]

688 mg (2.26 mmol) of tri-o-tolylphosphine and then 84 mg (0.37 mmol) of palladium(II) acetate are added to a vigorously stirred, degassed suspension of 12.7 g (37.7 mmol) of 9,10-dibromoanthracene, 17.2 g (97.7 mmol) of (5,6,7,8-tetrahydro-1-naphthyl)boronic acid and 26.6 g (126 mmol) of tripotassium phosphate in a mixture of 230 ml of toluene, 115 ml of dioxane and 170 ml of water, and the mixture is refluxed for 60 h. After cooling, the organic phase is separated off, washed three times with 200 ml of water and once with 200 ml of saturated, aqueous sodium chloride solution, dried over magnesium sulfate and evaporated to dryness under reduced pressure. The grey residue obtained in this way is recrystallised from dioxane. The deposited crystals are filtered off with suction, washed with 50 ml of ethanol and dried under reduced pressure; yield: 7.5 g, 45% having a purity of 99.8% according to HPLC.

The following compounds are prepared analogously to Examples 1 to 3:

-continued

| Example | Aryl bromide | Product |
|---|---|---|
| 7 | 9-bromo-10-(4-methylnaphthalen-1-yl)anthracene | corresponding product with bicyclic substituent |
| 8 | 9-bromo-10-(4-fluoronaphthalen-1-yl)anthracene | corresponding product with bicyclic substituent |
| 9 | 9-bromo-10-(4-tert-butylnaphthalen-1-yl)anthracene | corresponding product with bicyclic substituent |
| 10 | 9-bromo-10-(quinolin-4-yl)anthracene | corresponding product with bicyclic substituent |
| 11 | 9-bromo-10-(4-(trifluoromethyl)naphthalen-1-yl)anthracene | corresponding product with bicyclic substituent |
| 12 | 9-bromo-10-(di-p-tolylamino)anthracene | corresponding product with bicyclic substituent |

Example 13

9,10-Bis(1,1,4,4-tetramethyl-1,2,3,4-tetrahydro-8-methylnaphth-5-yl)anthracene a) 1,1,4,4-Tetramethyl-1,2,3,4-tetrahydro-8-methyl-naphthalene-5-boronic acid

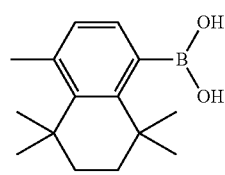 [SMILES: Cc1ccc(B(O)O)c2c1C(C)(C)CCC2(C)C]

Preparation analogous to Example 1a. Instead of 5-bromo-1,2,3,4-tetrahydro-1,4-methanonaphthalene, 56.2 g (200 mmol) of 5-bromo-1,1,4,4-tetramethyl-1,2,3,4-tetrahydro-8-methylnaphthalene are employed. Yield: 36.5 g (148 mmol), 74.1% of theory; purity: 98% according to $^1$H-NMR.

b) 9,10-Bis(1,1,4,4-tetramethyl-1,2,3,4-tetrahydro-8-methylnaphthalen-5-yl)anthracene

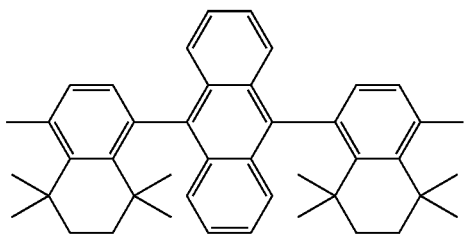

Preparation analogous to Example 1b. Instead of 21.6 g (115 mmol) of 1,2,3,4-tetrahydro-1,4-methanonaphthalene-5-boronic acid, 36.9 g (150 mmol) of 1,1,4,4-tetramethyl-1,2,3,4-tetrahydro-8-methylnaphthalene-5-boronic acid are used. Sublimation: $p=1\times10^{-5}$ mbar, 310° C. Yield: 15.9 g (27.5 mmol), 54.9% of theory; purity: 99.9% according to $^1$H-NMR, atropisomerically pure.

The following compounds are prepared analogously to Example 13:

| Example | Aryl bromide | Product |
|---|---|---|
| 14 | ![](aryl bromide 14) | ![](product 14) |
| 15 | ![](aryl bromide 15) | ![](product 15) |
| 16 | ![](aryl bromide 16) | ![](product 16) |

-continued

| Example | Aryl bromide | Product |
|---|---|---|
| 17 | 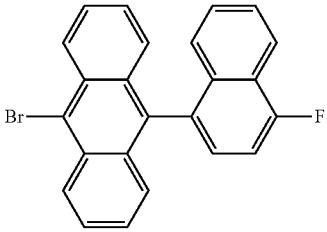 [SMILES: Fc1ccc(-c2c3ccccc3c(Br)c3ccccc23)c2ccccc12] | 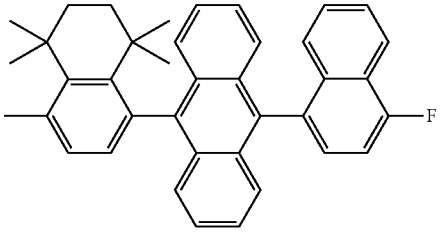 [SMILES: Cc1ccc(-c2c3ccccc3c(-c3ccc(F)c4ccccc34)c3ccccc23)c2c1C(C)(C)CCC2(C)C] |
| 18 | 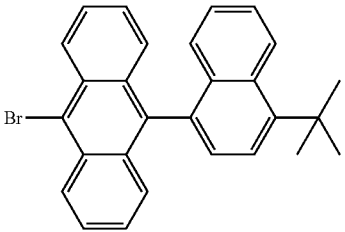 [SMILES: CC(C)(C)c1ccc(-c2c3ccccc3c(Br)c3ccccc23)c2ccccc12] | 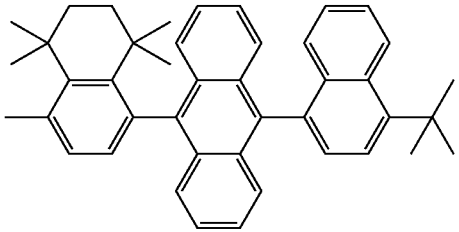 [SMILES: Cc1ccc(-c2c3ccccc3c(-c3ccc(C(C)(C)C)c4ccccc34)c3ccccc23)c2c1C(C)(C)CCC2(C)C] |
| 19 | 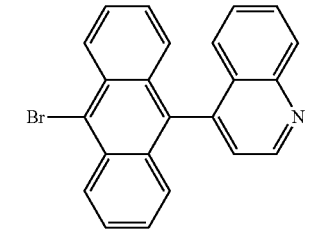 [SMILES: Brc1c2ccccc2c(-c2ccnc3ccccc23)c2ccccc12] | 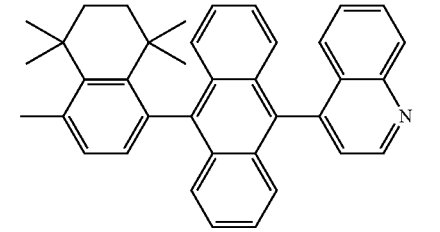 [SMILES: Cc1ccc(-c2c3ccccc3c(-c3ccnc4ccccc34)c3ccccc23)c2c1C(C)(C)CCC2(C)C] |
| 20 | 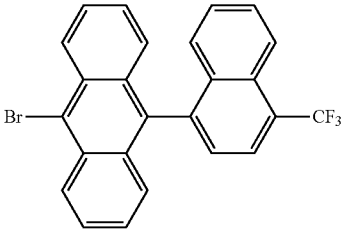 [SMILES: FC(F)(F)c1ccc(-c2c3ccccc3c(Br)c3ccccc23)c2ccccc12] | 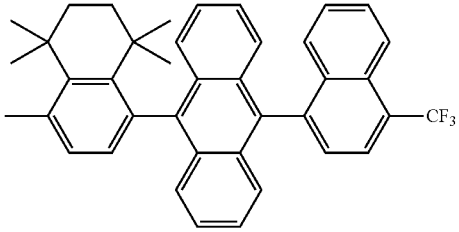 [SMILES: Cc1ccc(-c2c3ccccc3c(-c3ccc(C(F)(F)F)c4ccccc34)c3ccccc23)c2c1C(C)(C)CCC2(C)C] |
| 21 | 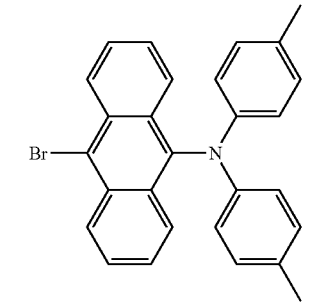 [SMILES: Cc1ccc(N(c2ccc(C)cc2)c2c3ccccc3c(Br)c3ccccc23)cc1] | 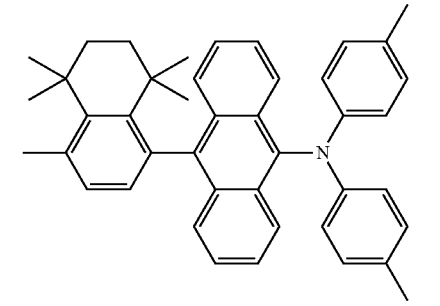 |

Example 22

Production of Fluorescent OLEDs Comprising Host Materials H1-H6 According to the Invention for Blue-electroluminescent OLEDs OLEDs are produced by a general process as described in WO 04/058911, which is adapted in individual cases to the particular circumstances (for example layer-thickness variation in order to achieve optimum efficiency or colour).

The results for various OLEDs are presented in Examples 23 to 42 below. The basic structure and the materials used (apart from the emitting layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTL1) | 20 nm 2,2',7,7'-tetrakis(di-para-tolylamino)-spiro-9,9'-bifluorene (vapour-deposited) |
| Hole-transport layer (HTL2) | 20 nm NPB (N-naphthyl-N-phenyl-4,4'-di-aminobiphenyl) |
| Emission layer (EML) | 30 nm layer of H1 to H7 as host material doped with x % (see table) of dopant E1 (vapour-deposited, synthesised as described in WO 06/000388) |
| Electron conductor (ETC) | 20 nm (vapour-deposited; AlQ$_3$ purchased from SynTec; tris(quinolinolato)-aluminium(III)) |
| Cathode | 1 nm LiF, 150 nm Al on top. |

The OLEDs can also be produced without PEDOT as hole-injection layer. In this case, the HTL1 then serves as hole-injection layer. Comparable results are obtained with these OLEDs.

These OLEDs are characterised by standard methods; for this purpose, the electroluminescence spectra, the efficiency (measured in cd/A) and the power efficiency (measured in lm/W) as a function of the brightness, calculated from current/voltage/brightness characteristic lines (IUL characteristic lines), are determined.

The host materials used (H1 to H7) and the emitter material used (E1) are listed below. The host H7 serves as comparative material in accordance with the prior art.

Emitter E1

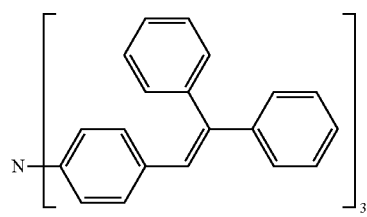

Host H1

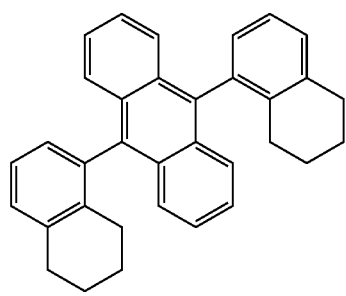

Host H2

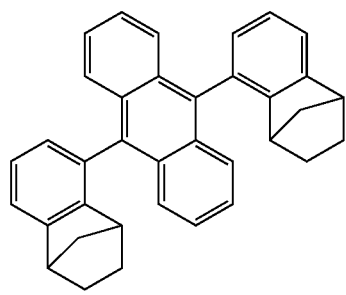

Host H3

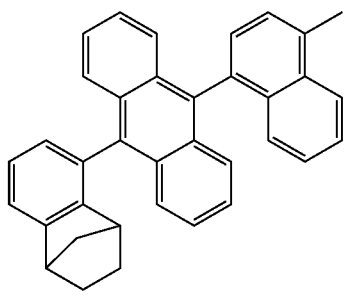

Host H4

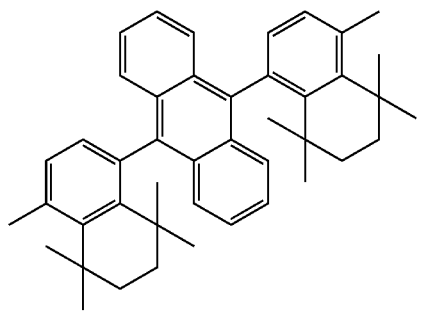

Host H5

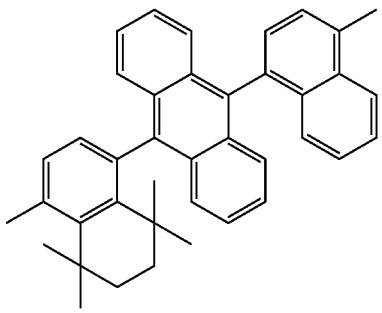

Host H6

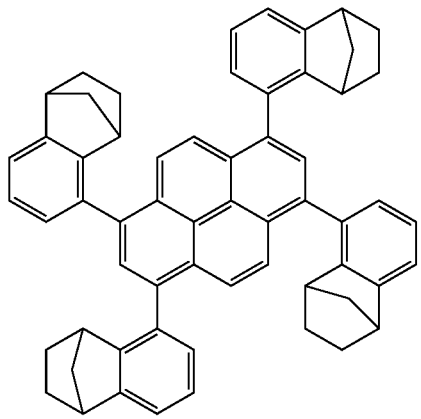

-continued

Host H7

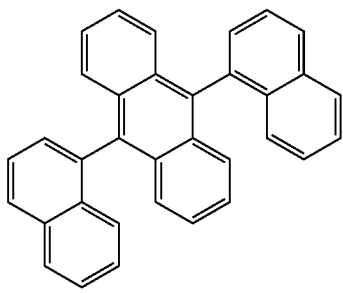

Table 1 shows the results for some OLEDs (Examples 23 to 42). As can be seen from the examples in Table 1, OLEDs comprising the host materials according to the invention (H1 to H6) in combination with emitter E1 exhibit efficient blue emission. Greater efficiency and a darker blue colour are obtained here than with di-1-naphthylanthracene in accordance with the prior art.

TABLE 1

| Example | EML | Max. efficiency (cd/A) | Voltage (V) at 1000 cd/m² | CIE |
|---|---|---|---|---|
| 23 | H1 5% E1 | 7.7 | 6.3 | x = 0.16; y = 0.25 |
| 24 | H1 3% E1 | 6.9 | 6.5 | x = 0.16; y = 0.21 |
| 25 | H2 3% E1 | 7.2 | 6.2 | x = 0.16; y = 0.21 |
| 26 | H2 5% E1 | 8.1 | 6.1 | x = 0.16; y = 0.25 |
| 27 | H2 7% E1 | 7.8 | 6.0 | x = 0.16; y = 0.27 |
| 28 | H3 3% E1 | 7.7 | 6.2 | x = 0.16; y = 0.22 |
| 29 | H3 5% E1 | 8.2 | 6.0 | x = 0.16; y = 0.25 |
| 30 | H3 7% E1 | 7.5 | 6.3 | x = 0.16; y = 0.26 |
| 31 | H4 3% E1 | 7.1 | 6.4 | x = 0.16; y = 0.22 |
| 32 | H4 5% E1 | 8.1 | 6.0 | x = 0.16; y = 0.25 |
| 33 | H4 7% E1 | 7.2 | 6.2 | x = 0.16; y = 0.29 |
| 34 | H5 3% E1 | 7.5 | 6.2 | x = 0.16; y = 0.22 |
| 35 | H5 5% E1 | 8.3 | 6.1 | x = 0.16; y = 0.25 |
| 36 | H5 7% E1 | 7.5 | 6.1 | x = 0.16; y = 0.28 |
| 37 | H6 3% E1 | 7.7 | 6.6 | x = 0.16; y = 0.29 |
| 38 | H6 5% E1 | 8.5 | 6.5 | x = 0.16; y = 0.32 |
| 39 | H6 7% E1 | 7.0 | 6.1 | x = 0.16; y = 0.33 |
| 40 (comparison) | H7 3% E1 | 6.3 | 6.9 | x = 0.16; y = 0.23 |
| 41 (comparison) | H7 5% E1 | 7.8 | 6.1 | x = 0.16; y = 0.28 |
| 42 (comparison) | H7 7% E1 | 6.5 | 6.0 | x = 0.16; y = 0.30 |

Example 43

Examples of OLEDs which comprise emitters according to the invention are shown below. Emitters E2 and E3 according to the invention used are listed below:

Emitter 2

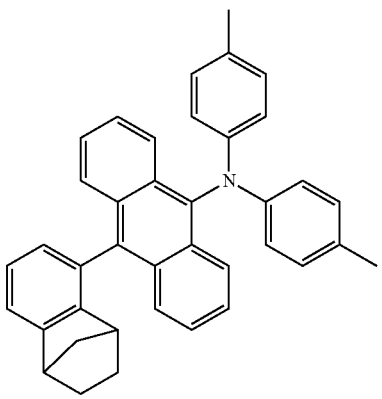

Emitter 3

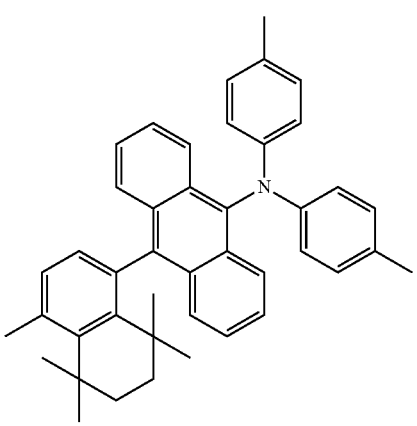

Table 2 shows the results for some OLEDs (Examples 44 to 50). As can be seen from the examples in Table 2, OLEDs comprising emitter E2 or E3 according to the invention exhibit good efficiencies and good blue colour coordinates. Furthermore, emitters E2 and E3 according to the invention have greater thermal stability than emitter E1 in accordance with the prior art.

TABLE 2

| Example | EML | Max. efficiency (cd/A) | Voltage (V) at 1000 cd/m² | CIE |
|---|---|---|---|---|
| 44 | H7 5% E2 | 6.5 | 6.5 | x = 0.16; y = 0.20 |
| 45 | H7 5% E3 | 6.6 | 6.4 | x = 0.16; y = 0.18 |
| 46 | H7 7% E3 | 6.8 | 6.3 | x = 0.16; y = 0.21 |
| 47 | H2 5% E2 | 6.8 | 6.4 | x = 0.15; y = 0.20 |
| 48 | H2 5% E3 | 6.9 | 6.5 | x = 0.16; y = 0.20 |
| 49 | H5 5% E2 | 6.7 | 6.4 | x = 0.16; y = 0.21 |
| 50 | H5 5% E3 | 6.8 | 6.3 | x = 0.16; y = 0.20 |

The invention claimed is:

1. A mixture comprising at least one compound of the Formula (I) and one or more dopants;

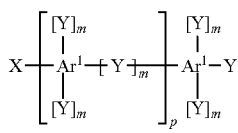

Formula (1)

wherein
Ar¹ is, identically or differently on each occurrence, a fused aryl or heteroaryl group having at least 14 aromatic ring atoms optionally substituted by one or more R;

X is, identically or differently on each occurrence, a group of formula (2) or (3)

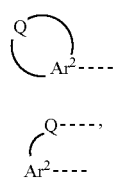

Formula (2)

Formula (3)

wherein the dashed bond is a link from $Ar^2$ or Q to $Ar^1$;

Y is, identically or differently on each occurrence, X; an $Ar^3$ group; or an $N(Ar^3)_2$ group, wherein the two $Ar^3$ radicals are optionally bonded to one another by a single bond or via an O, S, N(R), or $C(R)_2$ group;

$Ar^2$ is, identically or differently on each occurrence, an aryl or heteroaryl group optionally substituted by one or more R and to which a group Q is bonded, with the proviso that either the group Q or an R other than H is bonded in the orthoposition to the $Ar^1$—$Ar^2$ bond;

$Ar^3$ is, identically or differently on each occurrence, an aromatic or heteroaromatic ring system optionally substituted by one or more R;

Q is, identically or differently on each occurrence, a linear, branched, or cyclic alkylene or alkylidene group which forms two bonds to $Ar^2$ or one bond to $Ar^1$ and one bond to $Ar^2$ and thereby defining a further ring system; wherein Q has up to 20 C atoms optionally substituted by $R^1$, wherein one or more non-adjacent C atoms are optionally replaced by N—$R^1$, O, S, O—OO—O, CO—O, —$CR^1$=$CR^1$—, or—C≡C—, and one or more H atoms are optionally replaced by F, Cl, Br, I, or CN,
wherein Q is bonded to the ortho-position of $Ar^2$, where said ortho-position is relative to the link between $Ar^2$ and $Ar^1$;

R is, identically or differently on each occurrence, H, F, Cl, Br, I, CN, a straight-chain alkyl or alkoxy chain having up to 40 C atoms, or a branched or cyclic alkyl or alkoxy group having 3 to 40 C atoms, wherein said straight-chain alkyl or alkoxy chain or said branched or cyclic alkyl or alkoxy group are optionally substituted by $R^1$, wherein one or more non-adjacent C atoms are optionally replaced by N—$R^1$, O, S, O—CO—O, CO—O, —$CR^1$=$CR^1$—, or —C≡C—, and wherein one or more H atoms are optionally replaced by F, Cl, Br, I, CN, or an aromatic or heteroaromatic ring system having 5 to 40 aromatic ring atoms optionally substituted by one or more $R^1$, or a combination of two, three or four of these systems; and wherein two or more R here optionally define a further mono- or polycyclic, aliphatic, or aromatic ring system with one another;

$R^1$ is, identically or differently on each occurrence, H or a hydrocarbon radical having up to 20 C atoms, wherein said hydrocarbon radical is optionally aliphatic or aromatic or a combination of aliphatic and aromatic, and wherein one or more H atoms are optionally replaced by F;

m is, on each occurrence, 0 or 1;

p is, on each occurrence, 0, 1, or 2;

with the proviso that the following compound is excluded as a compound of formula (1):

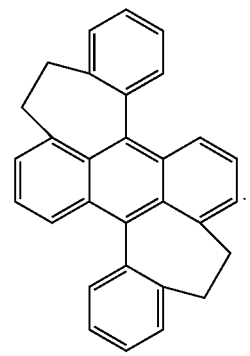 [SMILES: c1ccc2c(c1)CCc1cccc3c4c5c(cccc5c-2c13)CCc1ccccc1-4]

2. The mixture of claim 1, wherein said dopants are selected from the group consisting of aromatic anthracenamines, aromatic anthracenediamines, aromatic pyrenamines, aromatic pyrene-diamines, monostyrylamines, distyrylamines, tristyrylamines, tetrastyrylamines, styrylphosphines, styryl ethers, and arylamines.

3. The mixture of claim 2, wherein $Ar^1$ is selected from the group consisting of anthracene, acridine, phenanthrene, phenanthroline, pyrene, naphthacene, chrysene, pentacene, phenanthroline, and perylene, each of which is optionally substituted by R.

4. The mixture of claim 1, wherein $Ar^1$ contains three, four, five, or six aromatic or heteroaromatic units, which are in each case fused to one another via one or more common edges and are optionally substituted by R.

5. The mixture of claim 1, wherein the compound of formula (1) is selected from the group consisting of structures of formula (7), (8), (9), (10), (11), and (12):

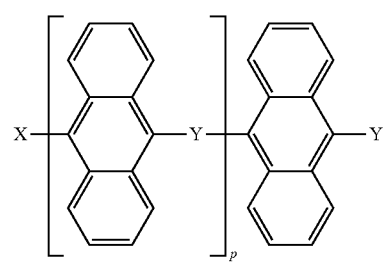

Formula (7)

Formula (8)

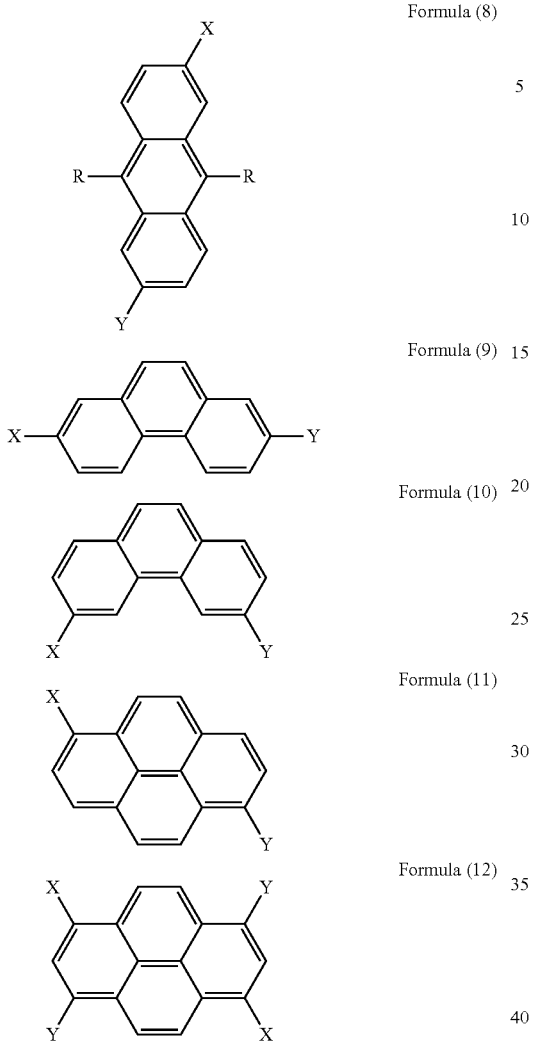

Formula (9)

Formula (10)

Formula (11)

Formula (12)

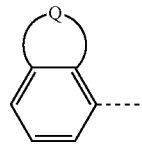 Formula (15)

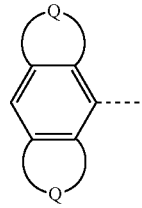 Formula (16)

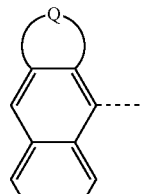 Formula (17)

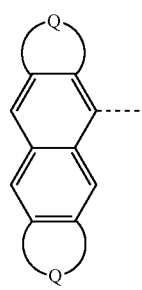 Formula (18)

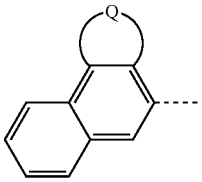 Formula (19)

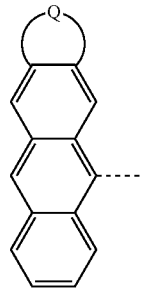 Formula (20)

wherein the anthracene, phenanthrene, and pyrene units are optionally substituted by one or more R.

6. The mixture of claim 1, wherein $Ar^3$ is, identically or differently on each occurrence, an aromatic or heteroaromatic ring system having 5 to 20 aromatic ring atoms optionally substituted by R.

7. The mixture of claim 1, wherein $Ar^2$, is, identically or differently on each occurrence, an aryl or heteroaryl group having 5 to 16 aromatic ring atoms optionally substituted by R.

8. The mixture of claim 1, wherein Q is a linear, branched, or cyclic alkylene chain having 2 to 15 C atoms optionally substituted by $R^1$, wherein one or more non-adjacent C atoms are optionally replaced by $N-R^1$, O, or S and one or more H atoms are optionally replaced by F or CN.

9. The mixture of claim 1, wherein Q defines a 6-, 7-, or 8-membered ring system together with $Ar^1$ and $Ar^2$ or defines a 3-, 4-, 5-, 6-, 7-, or 8-membered ring system together with $Ar^2$.

10. The mixture of claim 1, wherein the structures of formula (2) are selected from the group consisting of the structures of formula (15), (16), (17), (18), (19), and (20):

wherein the phenyl, naphthyl, or anthryl unit are in each case optionally substituted by R and wherein the dashed bond is the link to the $Ar^1$ unit.

11. The mixture of claim 1, wherein the structures of formula (2) are selected from the group consisting of the structures of formula (21), (22), (23), and (24):

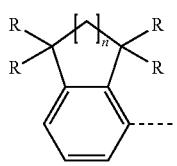

Formula (21)

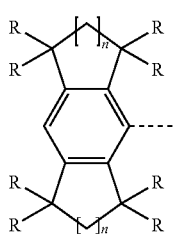

Formula (22)

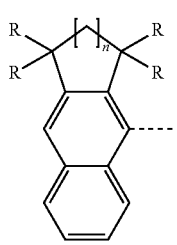

Formula (23)

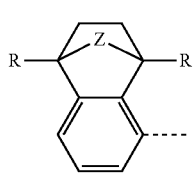

Formula (24)

wherein

Z is $CR_2$, O, S, NR, PR, P(=O)R, $SiR_2$, or $CR_2$—$CR_2$;

n is 1, 2, or 3; and the dashed bond is the link to the $Ar^1$ unit.

12. The mixture of claim 1, wherein Q defines a ring system with $Ar^2$.

13. The mixture of claim 1, wherein Q contains no benzylic protons or a bridgehead C atom is linked directly to $Ar^2$.

14. The mixture of claim 1, wherein p is 0 or 1.

15. The mixture of claim 1, wherein said compounds of the formula (I) are selected from structures (1) to (98):

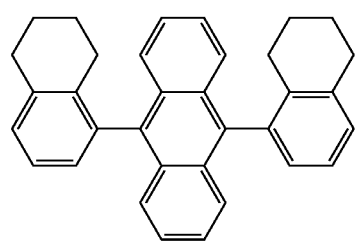

(1)

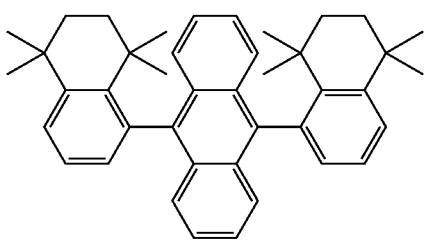

(2)

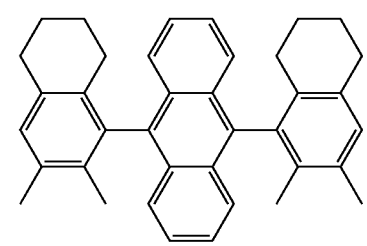

(3)

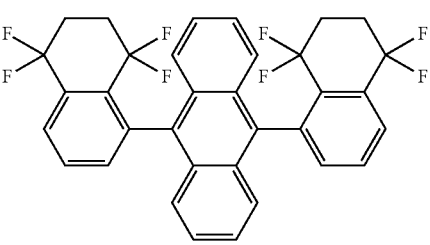

(4)

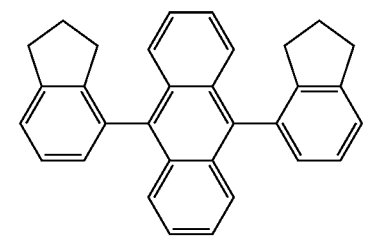

(5)

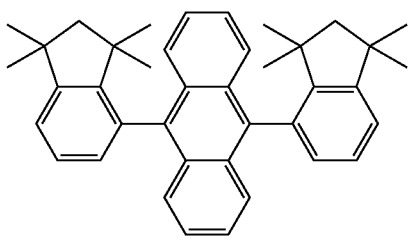

(6)

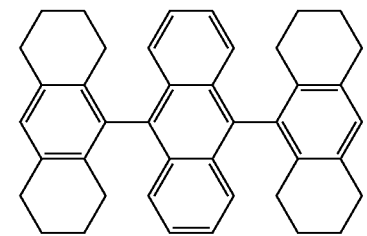

(7)

-continued
(8)
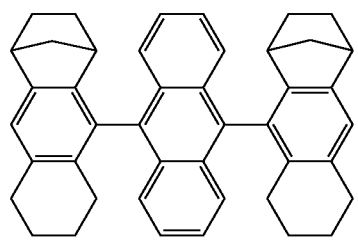
(9)
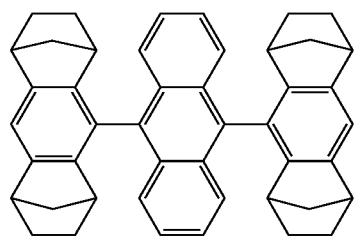
(10)
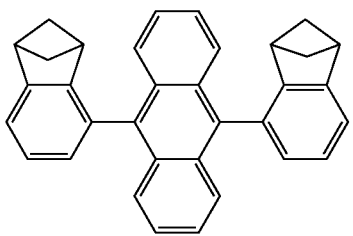
(11)
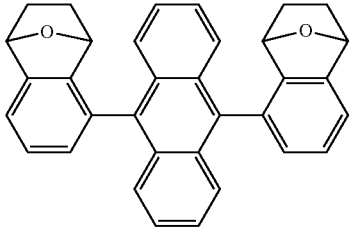
(12)
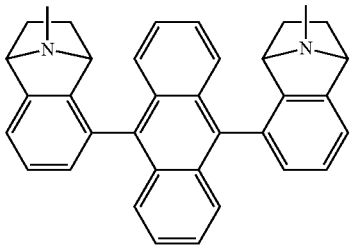
(13)
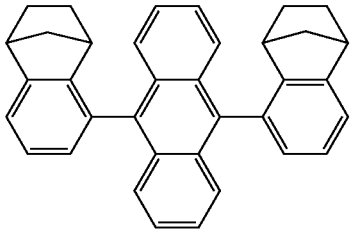
-continued
(14)
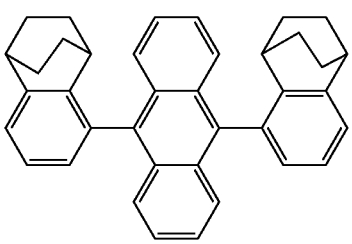
(15)
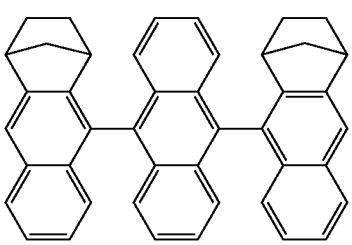
(16)
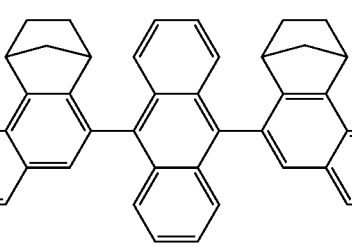
(17)
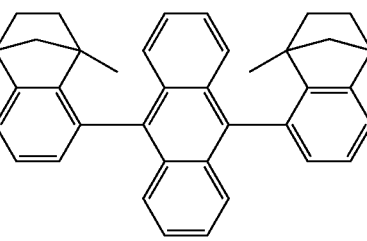
(18)
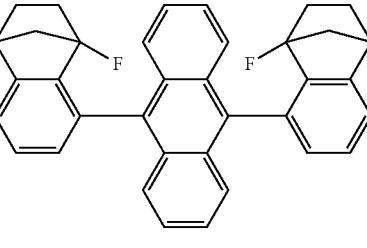
(19)
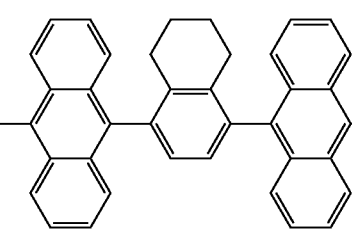

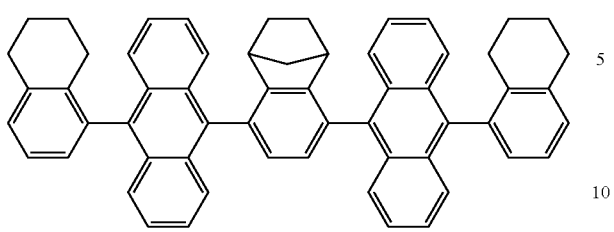
(20)
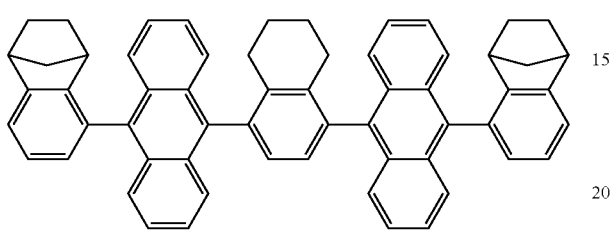
(21)
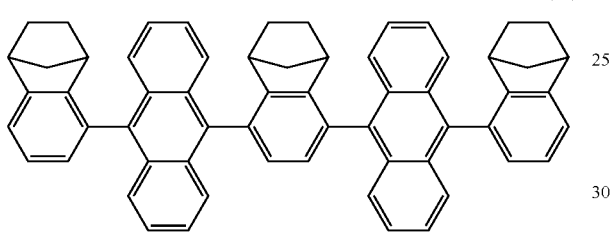
(22)
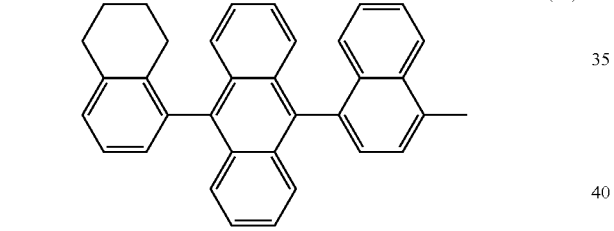
(23)
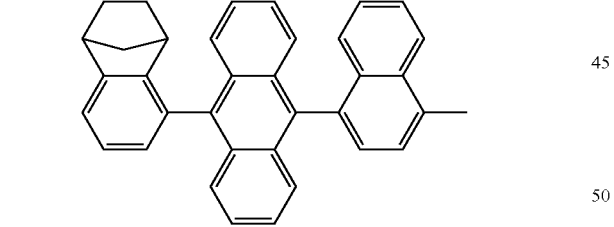
(24)
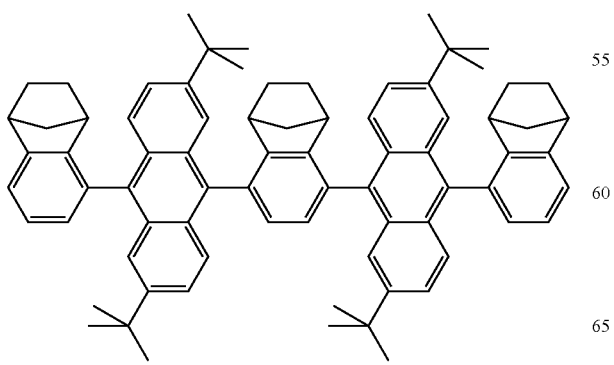
(25)
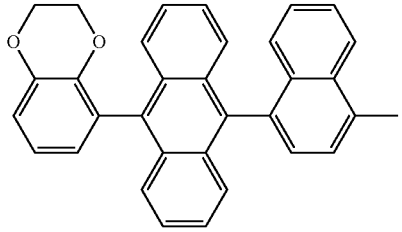
(26)
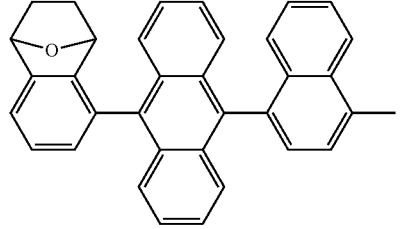
(27)
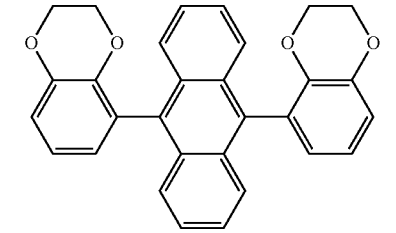
(28)
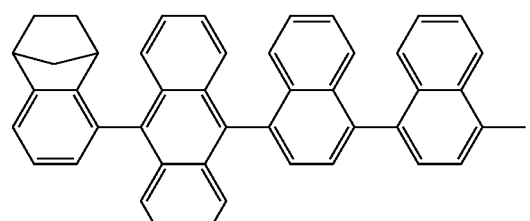
(29)
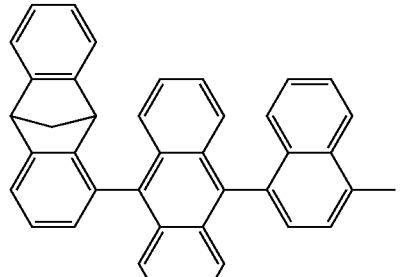
(30)
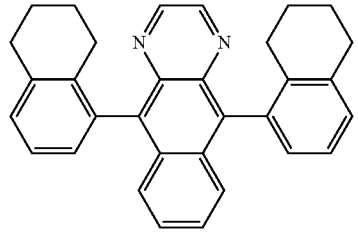
(31)

-continued
(32)
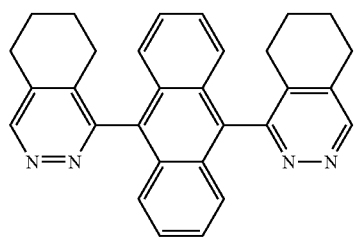
(33)
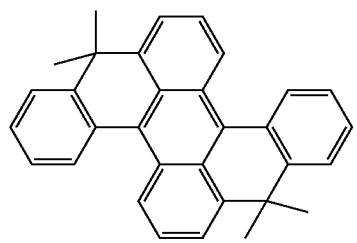
(34)
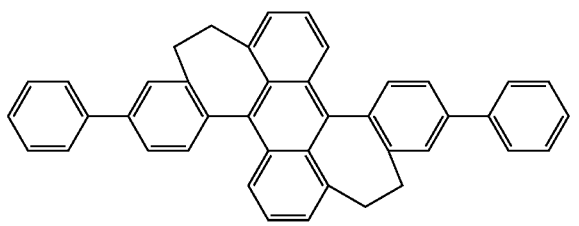
(35)
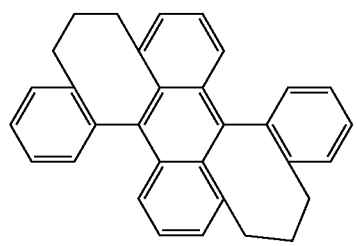
(36)
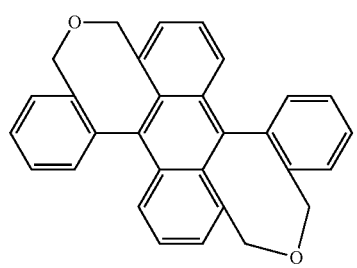
(37)
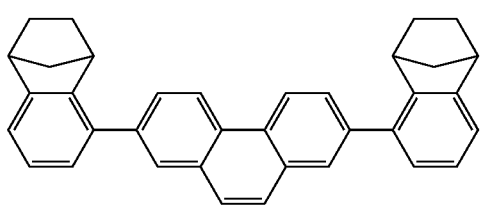
-continued
(38)
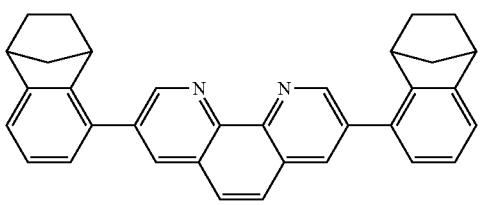
(39)
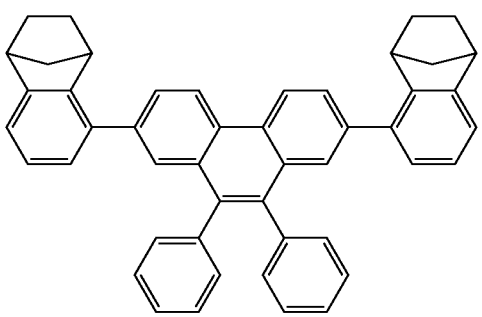
(40)
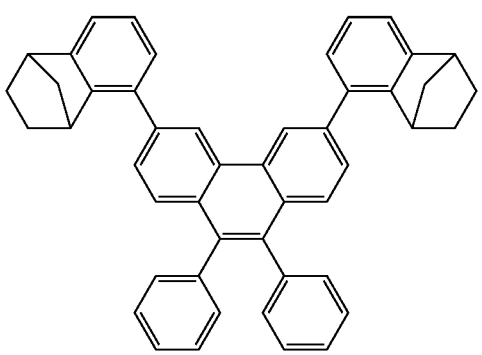
(41)
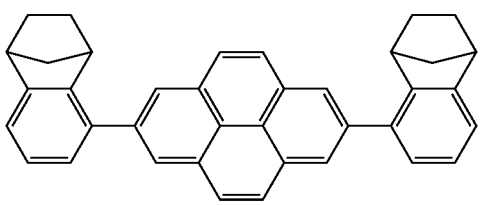
(42)
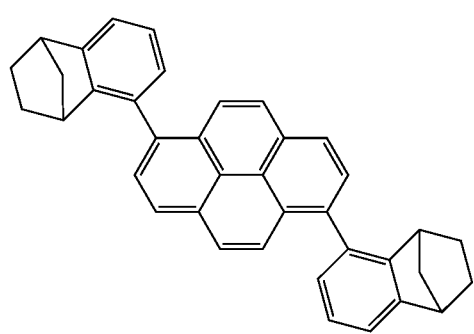

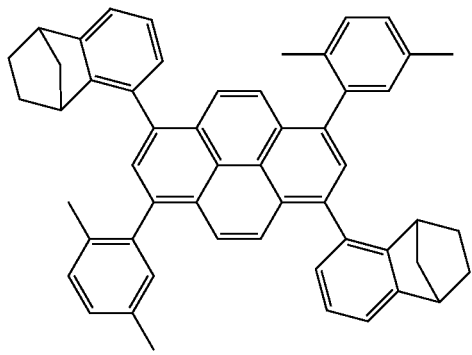 (43)
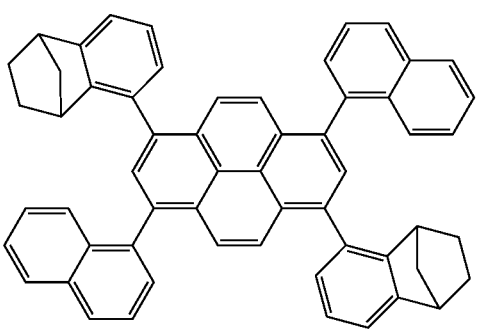 (44)
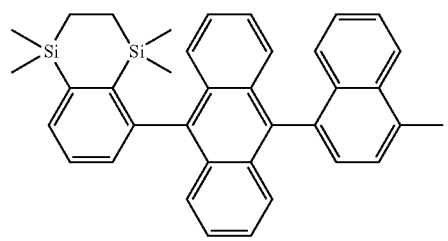 (45)
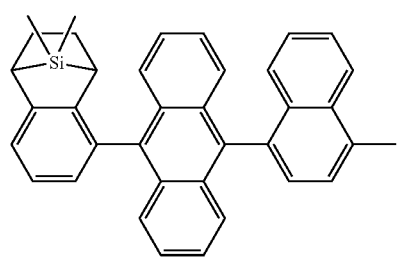 (46)
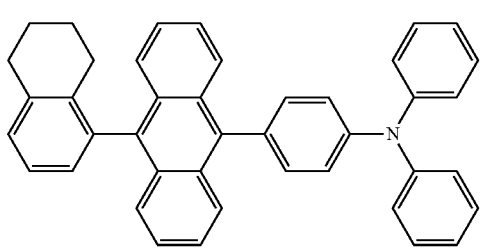 (47)
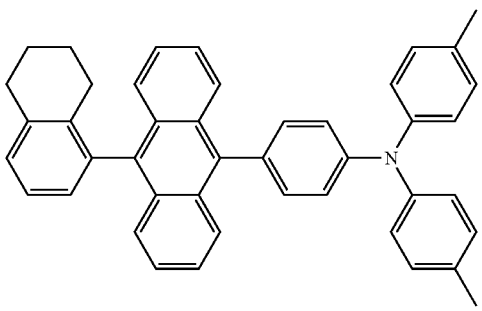 (48)
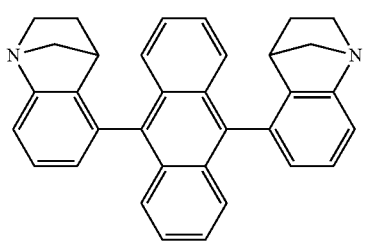 (49)
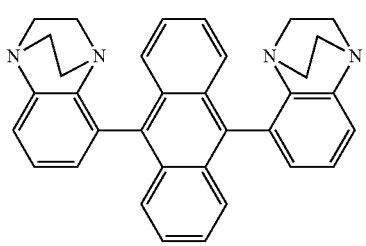 (50)
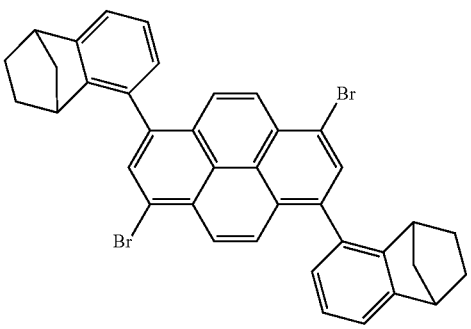 (51)
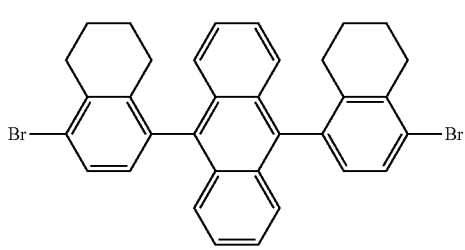 (52)

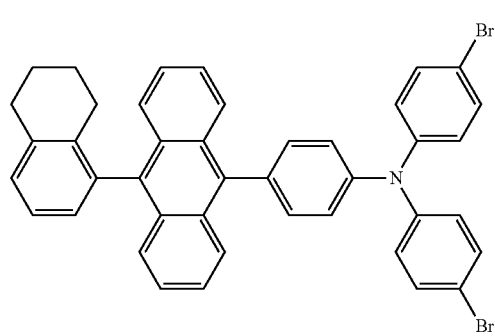
(53)
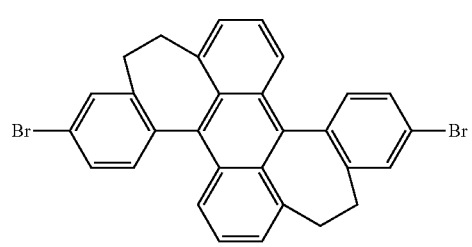
(54)
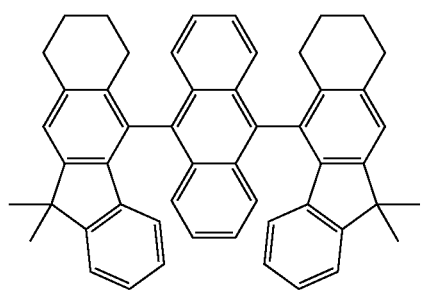
(55)
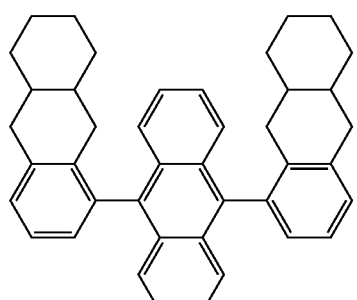
(56)
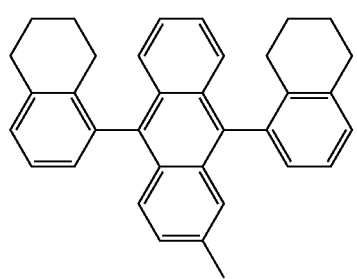
(57)
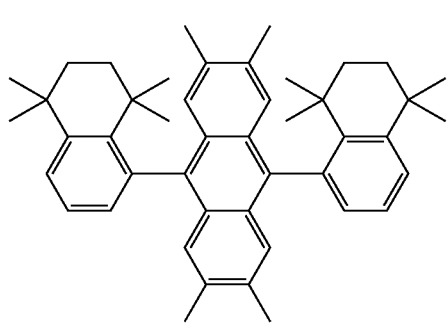
(58)
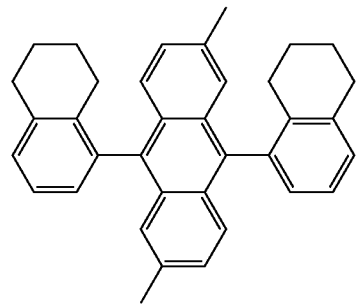
(59)
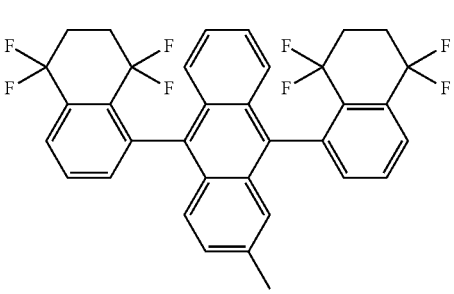
(60)
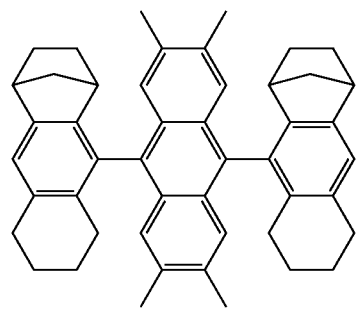
(61)
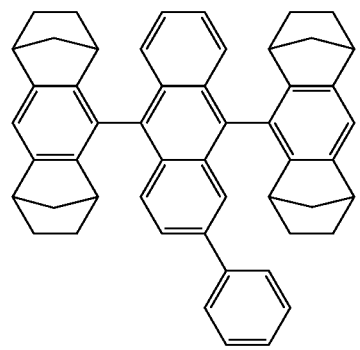
(62)

-continued
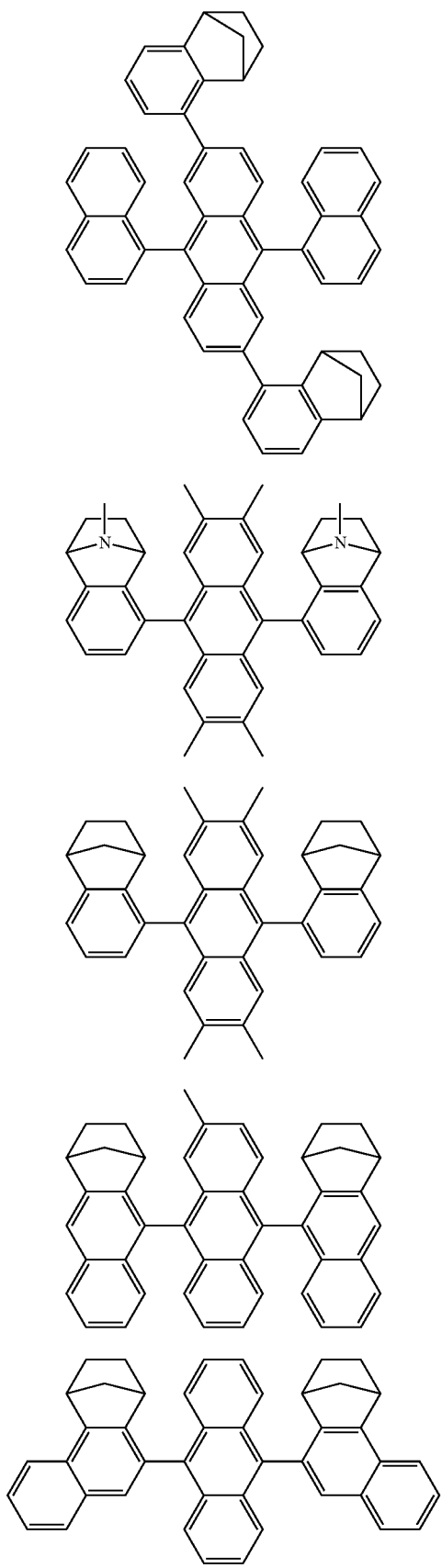
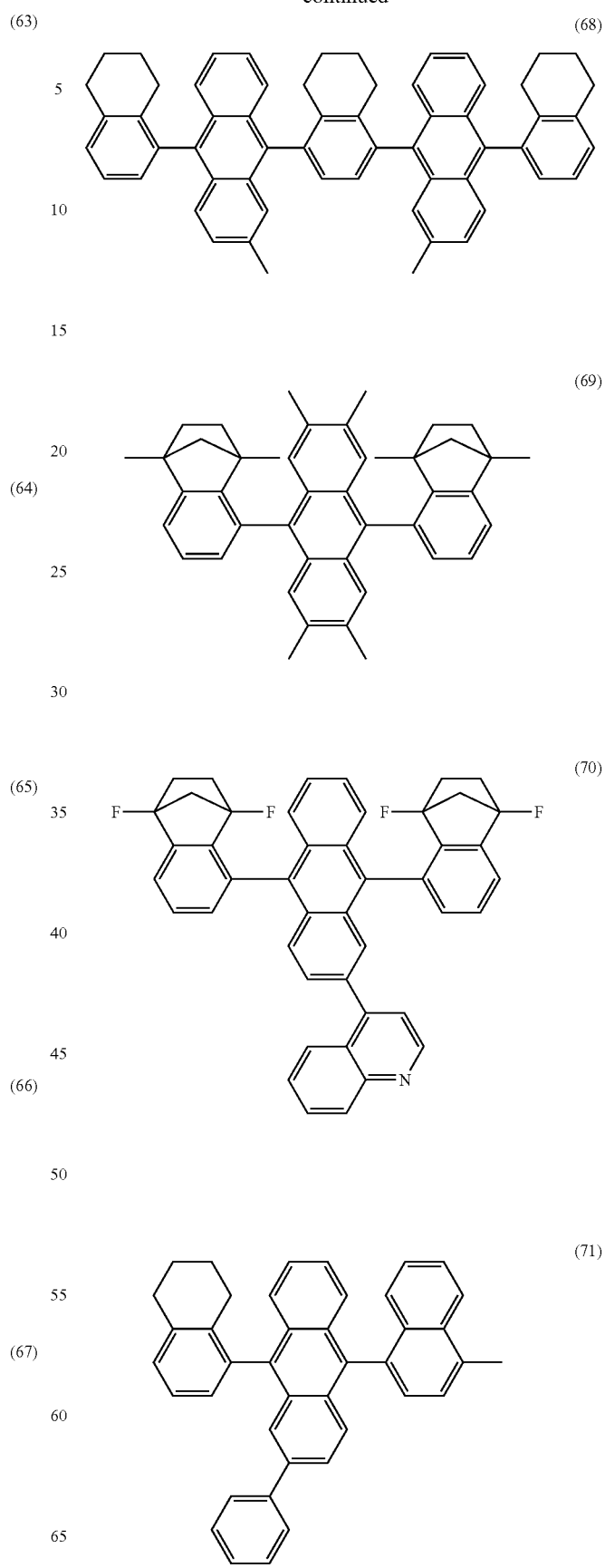

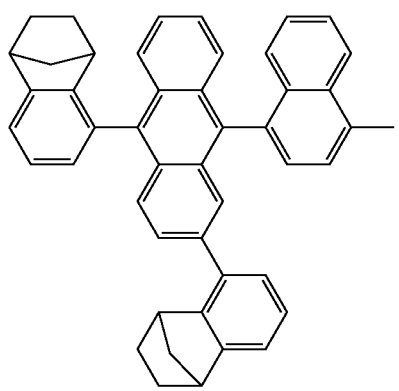
(72)
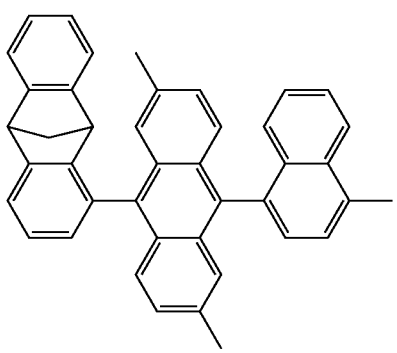
(76)
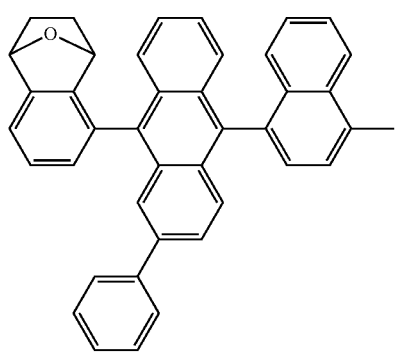
(73)
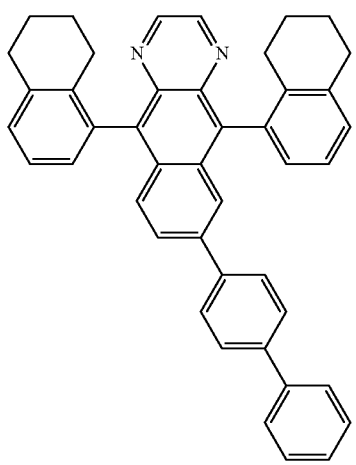
(77)
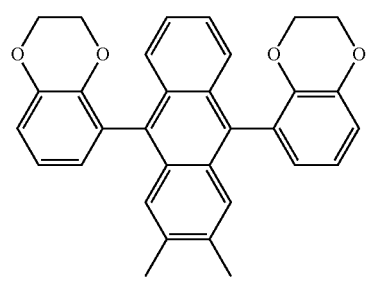
(74)
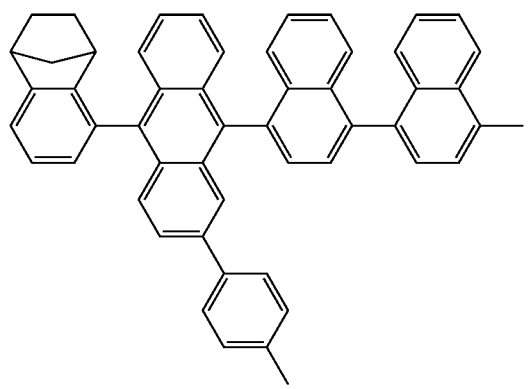
(75)
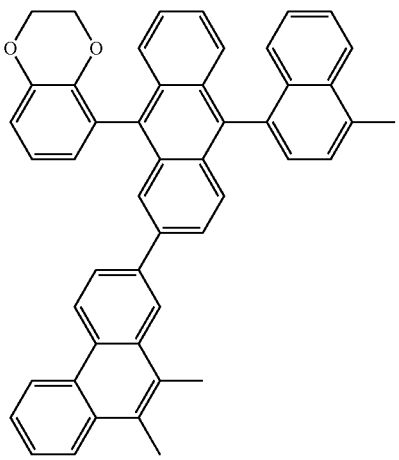
(78)

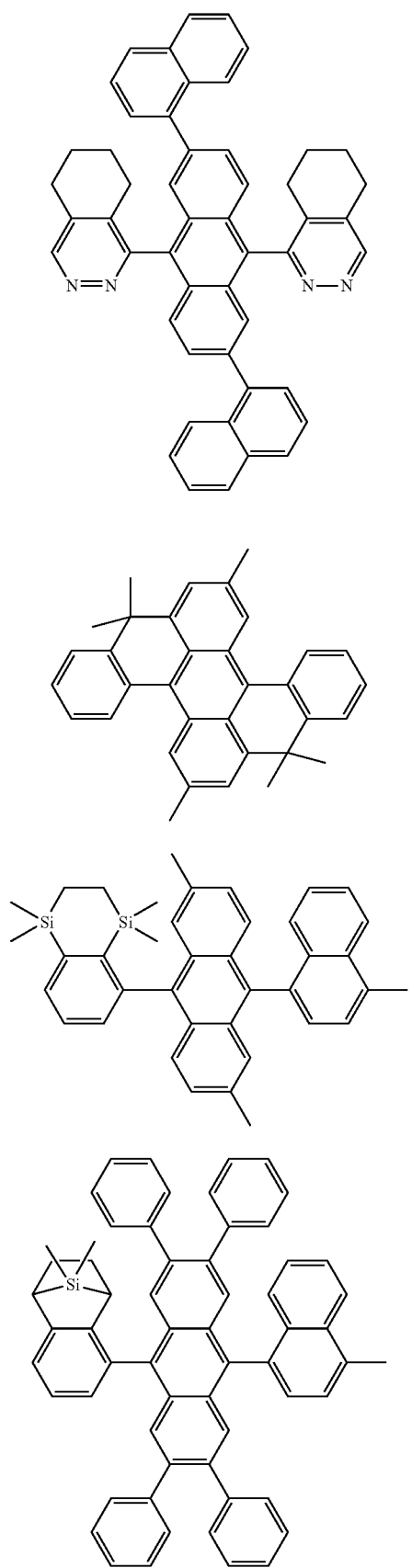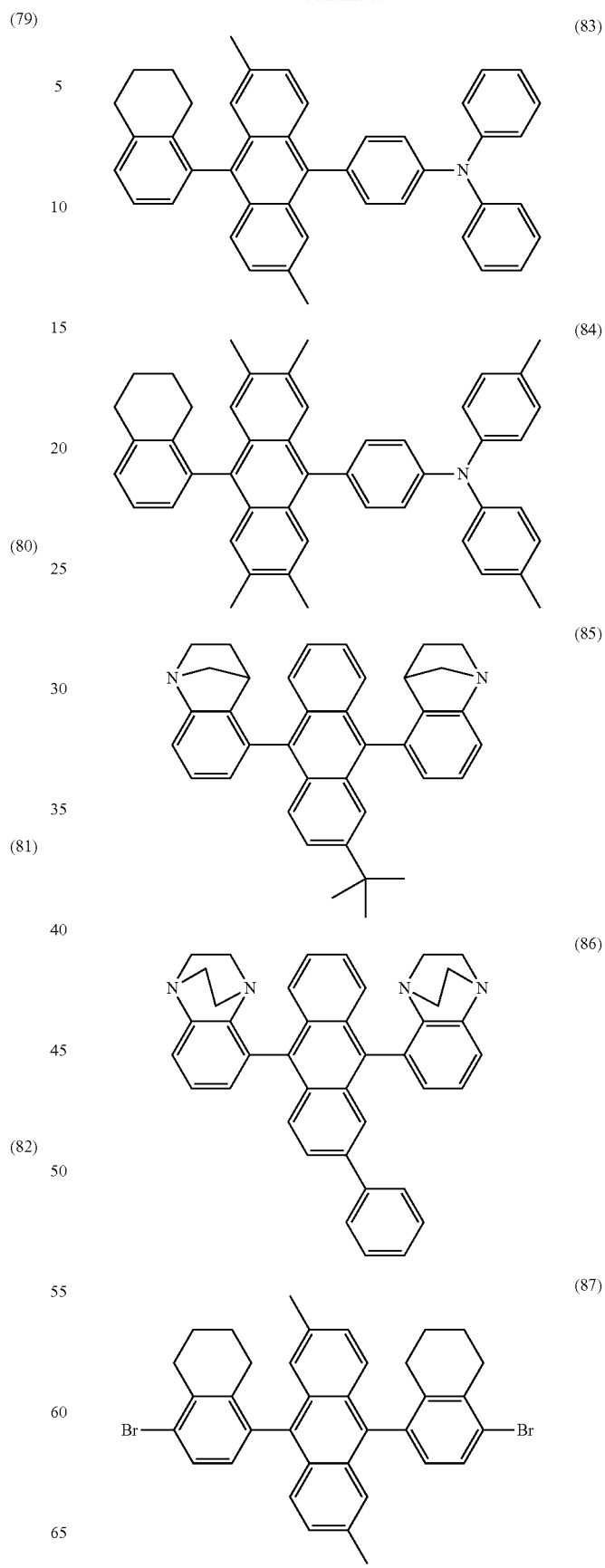

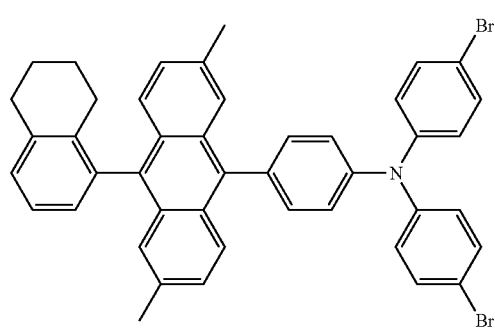
(88)
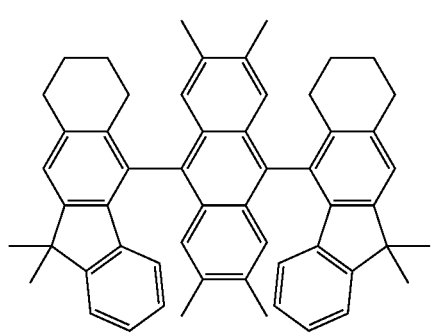
(89)
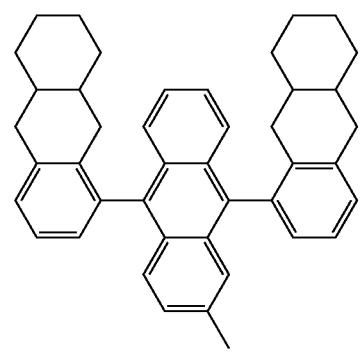
(90)
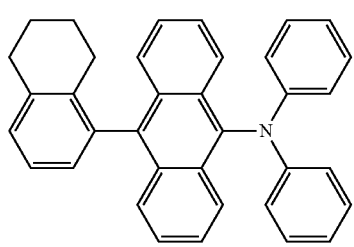
(91)
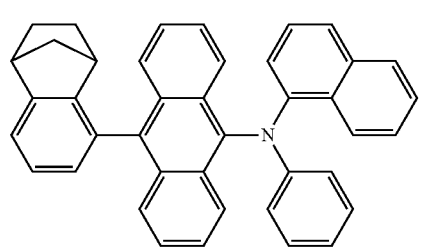
(92)
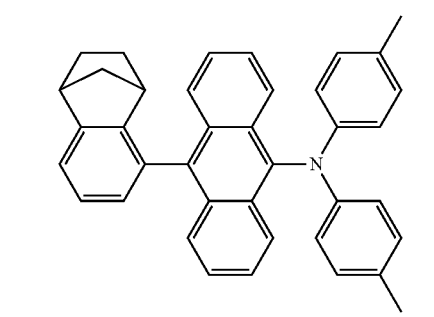
(93)
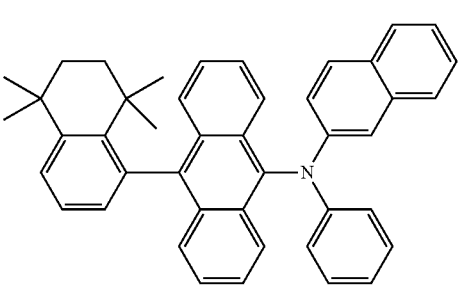
(94)
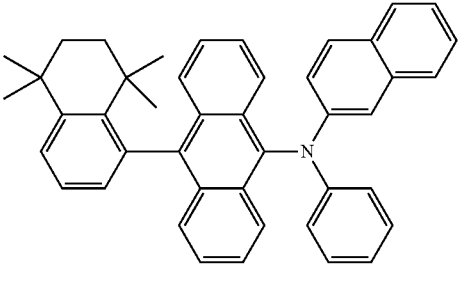
(95)
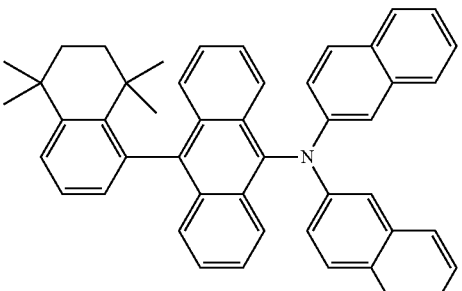
(96)
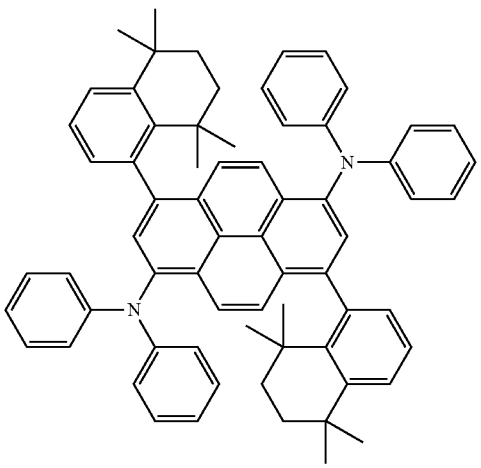
(97)

-continued
(98)
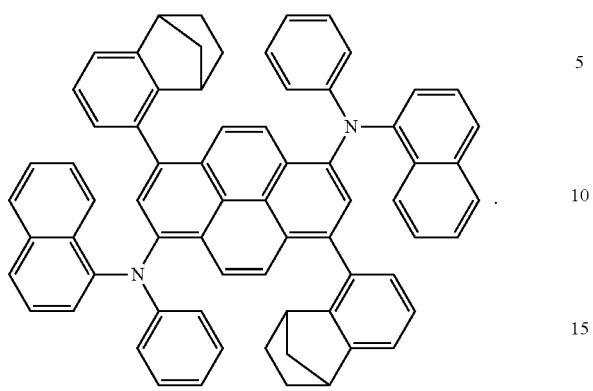
* * * * *